United States Patent [19]

Wand et al.

[11] Patent Number: 5,422,037

[45] Date of Patent: Jun. 6, 1995

[54] FERROELECTRIC LIQUID CRYSTAL COMPOUNDS CONTAINING HALOGENATED CORES AND CHIRAL HALOALKOXY TAIL UNITS

[75] Inventors: Michael Wand; Rohini Vohra; David Walba, all of Boulder, Colo.

[73] Assignee: Displaytech, Inc., Boulder, Colo.

[21] Appl. No.: 6,263

[22] Filed: Jan. 19, 1993

Related U.S. Application Data

[63] Continuation-in-part of Ser. No. 556,161, Jul. 20, 1990, Pat. No. 5,180,520, which is a continuation-in-part of Ser. No. 164,233, Mar. 4, 1988, Pat. No. 5,051,506.

[51] Int. Cl.$^6$ .................. C09K 19/52; C09K 19/12; C07D 239/02; C07D 19/26
[52] U.S. Cl. .................. 252/299.61; 252/299.01; 252/299.63; 252/299.64; 252/299.65; 252/299.66; 544/298; 546/346
[58] Field of Search .......... 252/299.01, 299.61, 252/299.62, 299.63, 299.64, 299.65, 299.66, 299.67; 544/245, 298, 335; 546/346

[56] References Cited

U.S. PATENT DOCUMENTS

| | | | |
|---|---|---|---|
| 4,728,458 | 3/1988 | Higuchi et al. | 252/299.65 |
| 5,130,048 | 7/1992 | Wand et al. | 252/299.01 |
| 5,167,855 | 12/1992 | Wand et al. | 252/299.01 |
| 5,180,520 | 1/1993 | Wand et al. | 252/299.61 |

FOREIGN PATENT DOCUMENTS 8705018  8/1987  WIPO .

OTHER PUBLICATIONS

Wand et al. "Properties of a Series of Phenylpyrimidine Ferroelectric Liquid Crystals Possessing the 2,3-difluoroalkoxy tail" (1991) Ferroelectrics 121:219–223.

*Primary Examiner*—Shean Wu
*Attorney, Agent, or Firm*—Greenlee and Winner

[57] ABSTRACT

The subject application discloses chiral nonracemic compositions of the general formula:

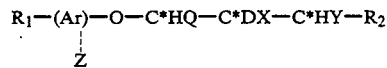

wherein $R_1$ is an achiral tail of two to sixteen carbons; Ar is an achiral FLC core of at least two rings; * denotes a chiral or potentially chiral carbon; Q and D are H or a methyl group, provided that q and D are not both methyl; X and Z are halides and Y is H or a halide; and $R_2$ is one to ten carbon atoms. The —O—C*H-Q—C*DX—C*HY— segment comprises the chiral proximal segment of the chiral tail. Z can be an ortho halide alone, or ortho and meta halides on adjacent carbons on the aromatic ring of the core adjacent to the proximal segment. $R_2$ is the distal segment of the chiral tail. The proximal segment is selected from the diastereomers and enantiomers:

| | |
|---|---|
| 2S-halo | 2R-halo |
| 1S-methyl-2S-halo | 1R-methyl-2R-halo |
| 1S-methyl-2R-halo | 1R-methyl-2S-halo |
| 2S,3S-dihalo | 2R,3R-dihalo |
| 2R,3S-dihalo | 2S,3R-dihalo |
| 1R-methyl-2R,3R-dihalo | 1S-methyl-2S,3S-dihalo |
| 1R-methyl-2R,3S-dihalo | 1S-methyl-2S,3R-dihalo |
| 1R-methyl-2S,3S-dihalo | 1S-methyl-2R,3R-dihalo |
| 1R-methyl-2S,3R-dihalo | 1S-methyl-2R,3S-dihalo |
| 2R-methyl-halo | 2S-methyl-halo. |

29 Claims, 3 Drawing Sheets

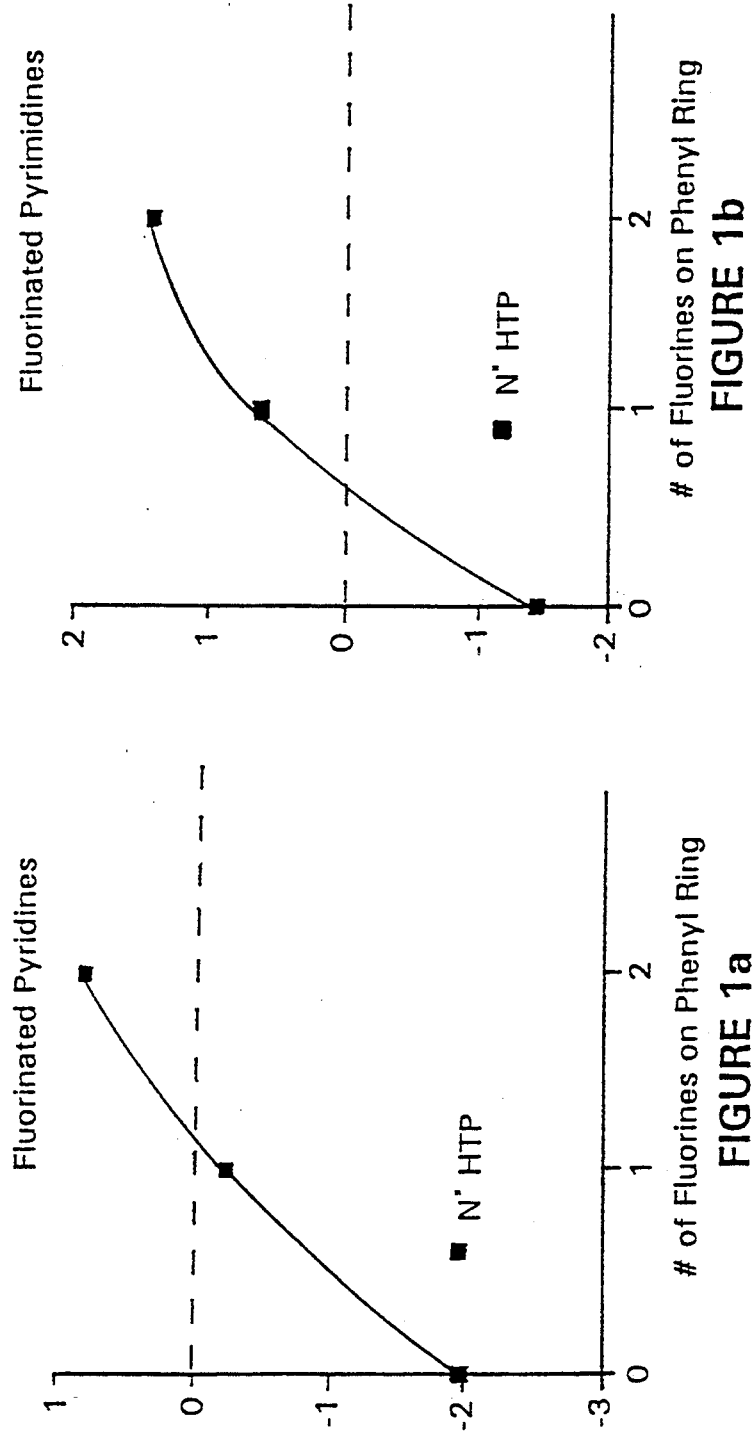

FERROELECTRIC LIQUID CRYSTAL COMPOUNDS CONTAINING HALOGENATED CORES AND CHIRAL HALOALKOXY TAIL UNITS

This invention was made with partial support of the United States Government under National Science Foundation Grant No. ISI8860992. The United States Government has certain rights in this invention.

RELATEDNESS OF THE APPLICATION

This application is a continuation-in-part of U.S. Ser. No. 556,161, filed Jul. 20, 1990, which is a continuation-in-part of U.S. Ser. No. 164,233, filed Mar. 4, 1988, which issued on Sep. 24, 1991 as U.S. Pat. No. 5,051,506. U.S. Ser. No. 556,161 now U.S. Pat. No. 5,180,520 and U.S. Pat. No. 5,051,506 are incorporated herein in their entirety by reference.

FIELD OF THE INVENTION

The present invention relates to ferroelectric liquid crystals useful in electro-optical and display device applications.

BACKGROUND OF THE INVENTION

Liquid crystals have found use in a variety of electro-optical and display device applications, in particular those which require compact, energy-efficient, voltage-controlled light valves such as watch and calculator displays. These devices are based upon the dielectric alignment effects in nematic, cholesteric and smectic phases of the liquid crystal compound in which, by virtue of dielectric anisotropy, the average molecular long axis of the compound takes up a preferred orientation in an applied electric field. Since the coupling to an applied electric field by this mechanism is rather weak, the resultant electro-optical response time may be too slow for many potential applications.

Liquid crystal displays have a number of unique characteristics, including low voltage and low power of operation, which makes them perhaps the most promising of the non-emissive electro-optical display candidates available with today's technology. However, slow response and insufficient nonlinearity can impose limitations for many potential applications. The requirement for speed may become especially important in proportion to the number of elements which have to be addressed in a device. This may result in increasingly impractical production costs for the potential use of such devices in flat-panel displays for use in video terminals, oscilloscopes, radar and television screens.

It has been shown by N. A. Clark and S. T. Lagerwall in Appl. Phys. Lett. 36:899 (1980) and in U.S. Pat. No. 4,367,924 that electro-optic effects with sub-microsecond switching speeds are achievable using the technology of ferroelectric liquid crystals (FLCs). Some display structures prepared using FLC materials, in addition to the high speed (about 1,000 times faster than currently used twisted nematic devices) reported by these investigators, also exhibit bistable, threshold sensitive switching, making them potential candidates for light modulation devices including matrix addressed light valves containing a large number of elements for passive displays of graphic and pictorial information, as well as for optical processing applications. A recent review of the applications of FLC devices is given by Lagerwall, S. T. and Clarke, N. A. (1989) Ferroelectrics 94:3–62.

Smectic C liquid crystal phases composed of chiral, nonracemic molecules possess a spontaneous ferroelectric polarization, or macroscopic dipole moment, deriving from a dissymmetry in the orientation of molecular dipoles in the liquid crystal phases (Myer et al. (1975) J. Phys. (Les Ulis, Fr) 36:L-69). The ferroelectric polarization density is an intrinsic property of the material making up the phase and has a magnitude and sign for a given material under a given set of conditions. In ferroelectric liquid crystal display devices, like those of Clark and Lagerwall, appropriate application of an external electric field results in alignment of the molecules in the ferroelectric liquid crystal phase with the applied field. When the sign of the applied field is reversed, realignment or switching of the FLC molecules occurs. This switching can be employed for light modulation. Within a large range of electric field strengths, the switching speed (optical rise time) is inversely proportional to applied field strength and polarization or dipole density ($\underline{P}$), and directly proportional to orientational viscosity. Fast switching speeds are then associated with FLC phases which possess high polarization density and low orientational viscosity.

A basic requirement for application of ferroelectric liquid crystals in such devices is the availability of chemically stable liquid crystal compounds or mixtures which exhibit ferroelectric phases (chiral smectic C) over a substantial temperature range about room temperature. In some cases, the ferroelectric liquid crystal compound itself will possess an enantiotropic or monotropic ferroelectric (chiral smectic C*) liquid crystal phase. Ferroelectric liquid crystal mixtures possessing smectic C* phases with useful temperature ranges can also be obtained by admixture of chiral, nonracemic compounds, designated ferroelectric liquid crystal dopants into liquid crystal host material (which may or may not be composed of chiral molecules). Addition of the dopant can affect the ferroelectric polarization density and/or the viscosity of the C* phase and thereby affect the switching speed. Desirable FLC dopants are molecules which impart high ferroelectric polarization density to an FLC material without significantly increasing the orientational viscosity of the mixture. The components of FLC mixtures can also be adjusted to vary phase transition temperatures or to introduce desired LC phases.

Thermotropic liquid crystal molecules typically possess structures which combine a rigid core coupled with two relatively "floppy" tails (see Demus et al. (1974) Flussige Kristalle In Tabellen, VEB Deutscher Verlag fur Grundstoffindustrie, Lebzig for a compilation of the molecular structures of LC molecules). FLC materials have been prepared by the introduction of a stereocenter into one of the tails, thus introducing chirality. The first FLC compound to be characterized was DOBAMBC (Meyer et al., Supra) which contains a 2-methylbutyl chiral tail. Pure DOBAMBC exhibits a smectic C* phase with a ferroelectric polarization of $-3$ nC/cm$^2$.

There are a number of reports of compounds containing phenylbenzoate, biphenyl, phenylpyrimidine and related cores coupled to chiral tail units which possess monotropic smectic C* phases displaying fast switching speeds at room temperature, or which can be employed as FLC dopants to induce high polarization and fast switching speeds when combined in mixtures with FLC host materials.

The following are exemplary reports of such FLC compounds:

Walba et al., U.S. Pat. No. 4,556,727 reports phenylbenzoates having non-racemic 2-alkoxy-1-propoxy tails. Eidman and Walba, U.S. Pat. No. 4,777,280 report chiral 1-cyanoalkoxy phenylbenzoates. Walba and Razavi, U.S. Pat. No. 4,695,650 report chirally asymmetric reverse ester phenylbenzoates having chiral 1-haloalkyl tail units.

Ohno et al. (1989) U.S. Pat. No. 4,795,587 refers to liquid crystal compounds exhibiting smectic C phases which contain a phenylpyridine core having the formula:

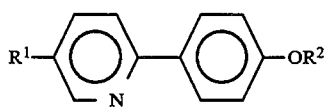

where $R^1$ is an alkyl group having seven to twelve carbon atoms and $R^2$ is an alkyl group having five to twelve carbon atoms.

Japanese patent documents JP 63264573 and JP 62258361 refer to optically active 6-substituted-pyridine-3-carboxylic acid esters useful as ferroelectric smectic liquid crystals. Optically active 6-substituted-pyridine-3-carboxylic acid esters obtained from reaction of dodecyloxybenzoic acid, thionyl chloride and 6-hydroxynicotinic acid (S)-2-methylbutyl ester are specifically referred to. Japanese patent document JP 62175465 refers to ester compounds contained in liquid crystal compositions exhibiting nematic phases. 2-(trans-4-ethyl-cyclohexyl)-5-nicotinic acid-3-fluoro-4-cyanophenyl ester is referred to specifically.

Walba et al. (1986) J. Amer. Chem. Soc. 108:7424-7425 and Walba and Vohra, U.S. Pat. Nos. 4,648,073 and 4,705,874 disclose ferroelectric (chiral) smectic liquid crystal compounds having an achiral core and chiral tail units derived from (2,3)-alkyloxiranemethanols which possess a high ferroelectric polarization density. The ferroelectric liquid crystal materials reported have the following general formulas:

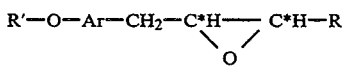

where R is an alkyl of one to seven carbon atoms and R' is an alkyl of five to twelve carbon atoms and Ar is phenylbenzoate or biphenyl.

Hemmerling et al. (1988) European Patent Application, Pub. No. 263437 refers to chiral aryl-2,3-epoxyalkylethers FLC compounds having phenylpyrimidine or phenylpyridazine cores of the formula:

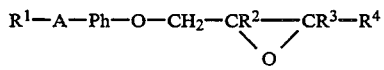

where A is a diazine-2,5,-diyl or diazine-3,6-diyl, $R^1$ is a straight chain or branched alkyl group having 1-12 carbon atoms wherein one or two non-neighboring $CH_2$ groups is replaced with an O or S atom, $R^{2-4}$ are, independent of one another, H, a straight chain alkyl group having 1-12 carbon atoms or a branched alkyl group having 3-10 carbon atoms wherein $R^1$, $R^2$ and $R^3$ are not all H. Compounds in which $R^2$ and $R^3$ are both H having extrapolated polarization densities ($\underline{P}_{ext}$) in the range from 30-70 $nC/cm^2$ are reported.

Walba and Razavi, U.S. Pat. No. 4,835,295, discloses chirally asymmetric phenyl and biphenylbenzoates having chiral 2,3-epoxy alkyl or 1-halo-2,3-epoxy alkyl tails which are useful as components of FLC materials. The compounds disclosed have the formula:

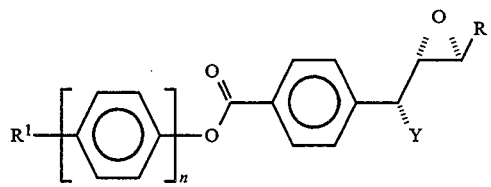

where R' is an alkyl or alkoxyl group having three to fifteen carbon atoms, R is an alkyl group having three to fifteen carbon atoms, n=1 or 2, and Y is a halogen or hydrogen. It is also disclosed, therein, that 1-haloepoxides of formula A can impart higher polarization densities and higher switching speeds in FLC mixtures than their diastereomers of formula B. It is suggested that the difference in properties of $\underline{A}$ and $\underline{B}$ is due to the relative alignment of the epoxide and halogen bond dipoles in the isomer.

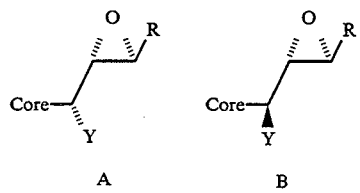

Furukawa, K. et al. (1988) Ferroelectrics 85:451-459 refers to chiral smectic C compounds having an ester group in the core and an optically active tail group, either alkoxy or alkoxy carbonyl, with an electronegative substituent, either a halogen or cyano group, ortho to the chiral tail, for example:

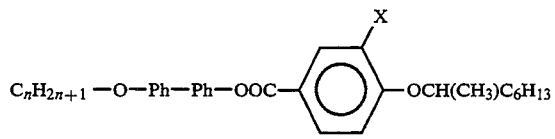

where X=H, Halogen or CN.

Wand et al., U.S. Ser. No. 360,397 discloses methyl epoxides having the formula

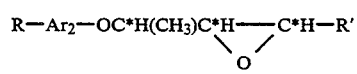

where $Ar_2$ is a phenylbenzoate, biphenyl phenylpyrimidine or phenyl pyridine, R is an alkyl or alkoxy group, and R' is an alkyl group containing 3 to 12 carbon atoms.

While a number of useful ferroelectric liquid crystal materials (both pure compounds and mixtures) have been reported, there is a growing need for FLC materials with varying properties of temperature range, tilt angle and switching speed for use in varied applications. Further, there is a need for FLC dopants with varying mixing properties (which are dependent, at least in part, on chemical composition) for use in the preparation of FLC mixtures. FLC dopants which impart high polarization density to, and retain low viscosity in, such mixtures are of particular interest.

SUMMARY OF THE INVENTION

The present invention provides a class of chirally asymmetric molecules which are useful as components of ferroelectric liquid crystal materials. The subject compounds can be useful as dopants in bistable SSFLC and/or deformed helix FLC (DHF) applications. The subject compounds can impart one or more properties to host materials. For example, the subject compounds can impart high ferroelectric polarization density and fast electro-optical switching speeds to low polarization materials when mixed with such materials to form ferroelectric liquid crystal compositions. Alternatively, certain of the compounds of the present invention can be used in pure form as they possess stable smectic C* phases having high polarization density.

In bistable SSFLC applications, large $P_s$ (spontaneous polarization density), fast rise time, low orientational viscosity, long N* pitch and long C* pitch are desirable. Large $P_s$, fast rise time, and low orientational viscosity all relate to the switching speed upon application of an optimal field. The N* and C* pitch are both manifestations of the chirality of the liquid crystal material. Although both are helices formed by the liquid crystal, the helices propagate in different directions and bring different complications to a FLC light modulator. The N* helix, in a surface stabilized FLC with planar geometry, runs perpendicular to the substrates, whereas in the same FLC, the C* helix runs parallel to the substrate. The N* helical repeat length or pitch, measured at the N→A or N→C transition, should be more than four times the width of the cell to give proper alignment of the FLC (Uchida, T. et al. (1989) Liquid Crystals 5:1127). Since good alignment is a prerequisite for SSFLC devices, a long N* pitch of the FLC composition is invariable desired. Thus, compounds of the subject invention can be useful in SSFLC applications either because they have both long N* and long C* pitch or because they have a C* or N* pitch that makes them useful as pitch compensating agents. A pitch compensating agent is a dopant compound that when mixed with other FLC compounds, adjusts the N* or C* pitch in the desired direction. For example, in an SSFLC application, a first FLC dopant with large $P_s$ but a short negative N* pitch can be compensated for with a second dopant having same sign $P_s$ and a positive N* pitch. As is known in the art, the positive N* pitch of the second dopant, when used in an appropriate quantity, will lengthen the negative N* pitch of the mixture, while the same sign $P_s$ will reenforce the negative $P_s$ of the first dopant.

The C* pitch can interfere with light as it passes through a cell, and can also interfere with alignment of the compounds between the surfaces. A C* pitch of the same or greater magnitude than the wavelength of modulated light passing through the SSFLC can give undesired diffraction patterns and discontinuity lines in the cell.

However, in deformable helix FLC (DHF) (Beresnev, L. S. et al. (1988) Ferroelectrics 85:173) applications, a very tight C* pitch, i.e., much less than the wavelength of the light, can be used for analog switching. By applying a sub-critical field to the DHF material, the C* helix can be deformed rather than unwound, resulting in a linear change in the apparent optic axis orientation, thus allowing analog light modulation. Thus, in materials to be used in a DHF cell, a tight C* pitch is desired. In DHF applications, a long N* pitch is preferred. Therefore, compounds having tight C* pitch in combination with either long N* pitch or inverted (in sign) N* pitch can be used for pitch compensation to lengthen the N* pitch.

The composition of the subject invention comprises chiral nonracemic compounds of the general formula:

$$R_1-(Ar)-O-C^*HQ-C^*DX-C^*HY-R_2$$
$$\phantom{R_1-(Ar)-O-C^*HQ-}|\phantom{DX-C^*HY-R_2}$$
$$\phantom{R_1-(Ar)-O-C^*HQ-D}Z$$

wherein:

$R_1$ is an achiral tail of two to sixteen carbons; Ar is an achiral FLC core of at least two rings; * denotes a chiral or potentially chiral carbon; Q and D are H or a methyl group, provided that Q and D are not both methyl groups; X and Z are halides and Y is H or a halide; and $R_2$ is one to ten carbon atoms. $R_2$ is the distal segment of the chiral tail. The —O—C*HQ—C*HX—C*HY— segment comprises the chiral proximal segment of the chiral tail; the proximal segment is selected from the diastereomers and enantiomers:

| | |
|---|---|
| 2S-halo | 2R-halo |
| 1S-methyl-2S-halo | 1R-methyl-2R-halo |
| 1S-methyl-2R-halo | 1R-methyl-2S-halo |
| 2S,3S-dihalo | 2R,3R-dihalo |
| 2R,3S-dihalo | 2S,3R-dihalo |
| 1R-methyl-2R,3R-dihalo | 1S-methyl-2S,3S-dihalo |
| 1R-methyl-2R,3S-dihalo | 1S-methyl-2S,3R-dihalo |
| 1R-methyl-2S,3S-dihalo | 1S-methyl-2R,3R-dihalo |
| 1R-methyl-2S,3R-dihalo | 1S-methyl-2R,3S-dihalo |
| 2R-methyl-halo | 2S-methyl-halo. |

The preferred proximal segments are:

| | |
|---|---|
| 2S-halo | 2R-halo |
| 1S-methyl-2S-halo | 1R-methyl-2R-halo |
| 2S,3S-dihalo | 2R,3R-dihalo |
| 1S-methyl-2R,3R-dihalo | 1R-methyl-2S,3S-dihalo |
| 2R-methyl-halo | 2S-methyl-halo. |

The achiral cores are rigid, linear moieties. Preferred cores are those that are chemically stable and which do not impart high orientational viscosity in the liquid crystal phase. In the present invention, cores containing at least two aromatic rings are preferred such as those cores based on phenylbenzoate, biphenylbenzoate, phenylpyrimidine, biphenylpyrimidine, phenylpyridine, biphenylpyridine or biphenyl structures. As used herein "phenylbenzoate" includes forward and reverse phenylbenzoates:

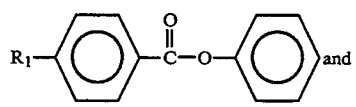

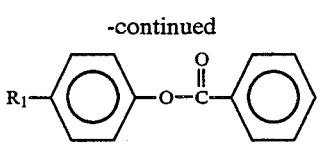

"Phenylpyrimidine" means 2,5-substituted phenylpyrimidines. Additionally, "phenylpyridine" means 2,5-substituted phenylpyridines.

Each of the cores of the present invention are halogenated in the aromatic ring adjacent to the chiral tail. Halogenation is either at a single ortho position or at one ortho and one meta position on adjacent carbons on the same side of the ring. When referring to the location of the halide(s), "ortho" and "meta" mean relative to the chiral tail. For example, the positions of halides on the aromatic ring adjacent to the chiral tail can be as follows:

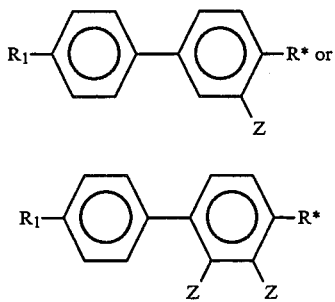

$R_1$ is the achiral tail and $R^*$ indicates the chiral tail, including the proximal and distal ($R_2$) segments. The chiral tail is positioned at the para position on its aromatic ring relative to the bond of its ring to the adjacent ring or to carbon or oxygen atoms bridging its ring to the adjacent ring. Likewise, the achiral tail is positioned at the para position on its aromatic ring relative to the bond of its ring to the adjacent ring or to carbon or oxygen atoms bridging its ring to the adjacent ring. For example, in a biphenyl core, the chiral and achiral tails are positioned 4,4'.

If there is both a meta and ortho halide on the core, they can be the same or different halides. The symbol Z can mean an ortho halide alone, or ortho and meta halides on adjacent carbons; in the latter case, the halide in the ortho position can be different than that in the meta position.

Table 1 illustrates some of the preferred and less preferred ferroelectric (FLC) cores useful in synthesizing the compounds of the subject invention. Cores comprising a pyridine or pyrimidine ring are preferably designed with the nitrogens in rings non-adjacent to the chiral tail. Again, Z indicates a halide or halides located on the ring either in one ortho position alone or at one ortho and one meta position on adjacent carbons.

The achiral tail, $R_1$, can be an alkyl, alkenyl or alkoxy group. $R_1$ can contain two to sixteen carbon atoms; it preferably contains five to sixteen carbons; and it most preferably contains eight carbons. $R_1$ can be straight chain or branched. Branching can broaden the smectic C* phase of the compound itself or of an FLC mixture containing the compound. The branching effect is enhanced when branching is more distant from the core. It has also been observed that if branching occurs at carbons 2–8 (relative to the core), the polarization density of the FLC molecule is generally not significantly affected.

As described in PCT/EP88/00724 (WO 02425, p.13), oxygen or sulfur atoms can replace non-adjacent $CH_2$ groups in the achiral tail to produce, for example, alkoxy or thioalkyl tails. It has been observed that such substitutions do not significantly impair the polarization density; such substitutions can impart a broader smectic C* phase of the compound itself or in an FLC mixture containing the compound.

When $R_1$ is an alkenyl, the double bonds can be located at any position in $R_1$'s chain, including the omega position. Positioning of a double bond in the omega position creates a precurser to an FLC polymer. For example, an FLC compound of the subject invention containing omega-alkenyl achiral tails could be reacted with polysiloxane to form a polymeric FLC.

TABLE 1

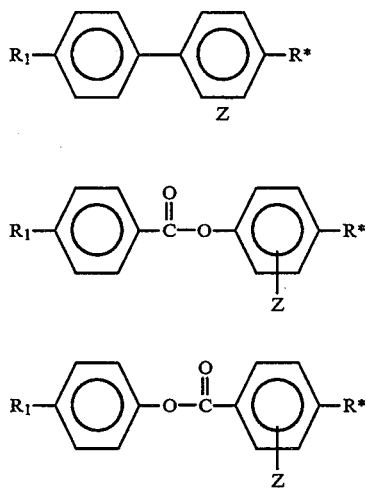

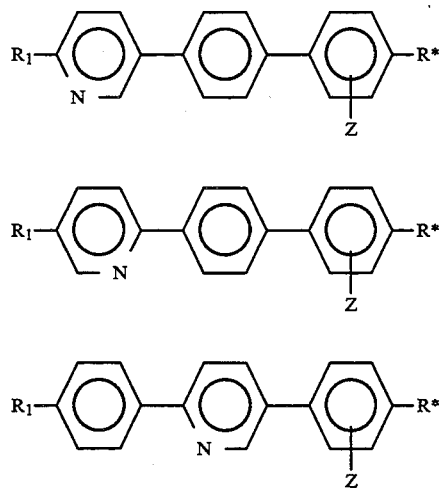

TABLE 1-continued
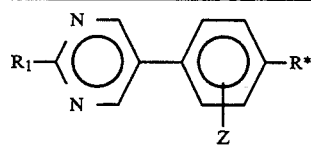
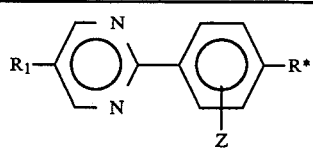
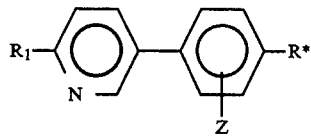
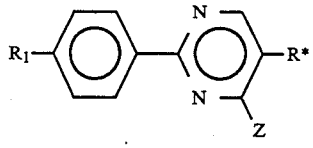
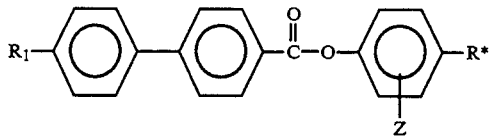
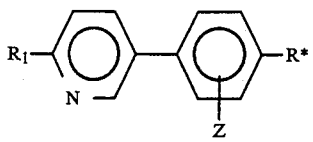
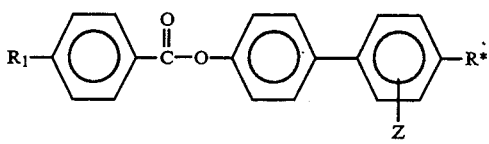
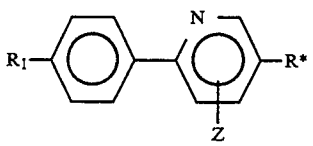
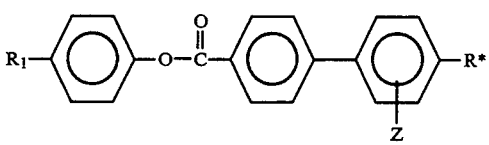
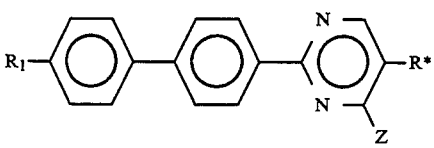
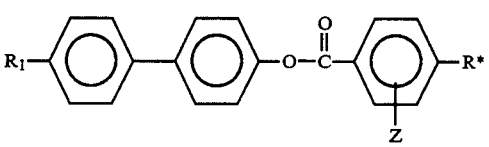
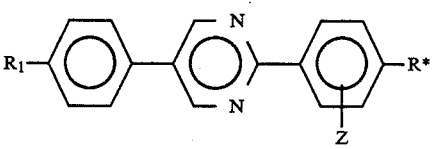
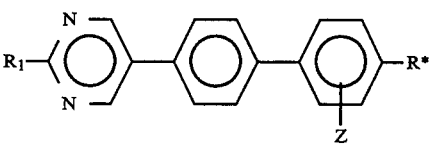
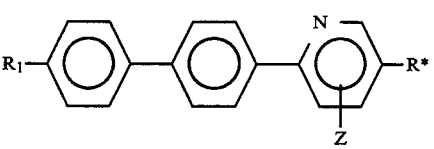
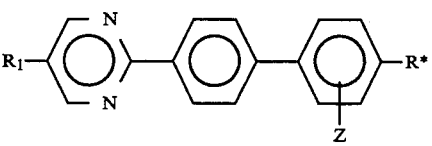
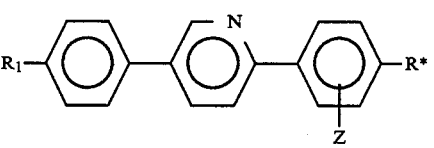
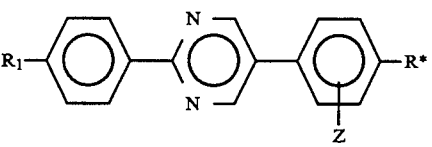
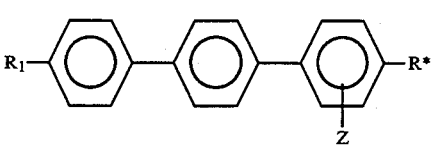
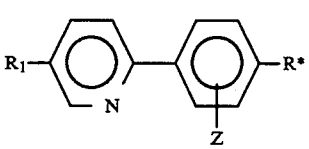
When $R_1$ is an alkenyl, the double bonds can be cis or trans. However, trans bonds are preferred because cis is likely to result in reduced solubility of the dopant FLC in the host material. Additionally, cis bonds can narrow the smectic C* range of the compound itself or of an FLC mixture containing the compound.

The halides of the chiral proximal segment are preferably fluorine and chlorine. X, Y and Z can be the same or different halides.

It has been observed that FLC dopants comprising one enantiomer of an enantiomer pair, such as:

| Enantiomer Pairs | | |
|---|---|---|
| 2S-halo | and | 2R-halo |
| 1S-methyl-2S-halo | and | 1R-methyl-2R-halo |
| 1S-methyl-2R-halo | and | 1R-methyl-3S-halo |
| 2S,3S-dihalo | and | 2R,3R-dihalo |
| 2R,3S-dihalo | and | 2S,3R-dihalo |
| 1R-methyl-2R,3R-dihalo | and | 1S-methyl-2S,3S-dihalo |
| 1R-methyl-2R,3S-dihalo | and | 1S-methyl-2S,3R-dihalo |
| 1R-methyl-2S,3S-dihalo | and | 1S-methyl-2R,3R-dihalo |
| 1R-methyl-2S,3R-dihalo | and | 1S-methyl-2R,3S-dihalo |
| 2R-methyl-halo | and | 2S-methyl-halo | function equivalently in FLC host materials as the FLC dopant comprising the other enantiomer of the enantiomer pair, except that the sign of their polarization densities is reversed. As will be understood by those in the art, the sign of the polarization of an FLC dopant should be the same as that of the host material in order to achieve high polarization mixtures. It is a feature of this invention that either enantiomer of the above-identified enantiomer pairs can be prepared. This allows choice of the appropriate enantiomers for use with a particular host material.

The distal segment ($R_2$) of the chiral tail of the compound of the subject invention can be an alkyl or alkenyl group of one to ten carbons. As the size of the distal segment increases, it can increase the viscosity of the FLC compound; for this reason, it is preferred that $R_2$ contain two to three carbons.

$R_2$ can be straight chain or branched. Branching can broaden the smectic C* phase; generally, this effect is enhanced when branching is more distant from the core.

If $R_2$ is an alkenyl, the double bonds can be located at any position in the segment. If $R_2$ contains double bonds, they may be cis or trans. However, trans bonds are preferred because cis bonds are likely to result in reduced solubility of the dopant FLC in the host material. Additionally, cis bonds are likely to narrow the smectic C* range of the compound itself or of an FLC mixture containing the compound.

$R_2$ can contain chiral carbons. Chirality in the distal segment, like that in the proximal segment, contributes to polarization density of the FLC molecule. The distal segment chirality can enhance or reduce the polarization density of the FLC molecule as imparted by the proximal segment. The closer the chiral groups in the distal segment to the proximal segment, the greater the impact of the $R_2$ chirality on the dipole created by the proximal segment. Whether a particular chiral $R_2$ enhances or decreases polarization density can be determined by routine testing by known methods of FLC compounds containing the chiral $R_2$ in question. Synthesis methods of $R_2$-containing FLC compounds of the subject invention are described hereinbelow and/or are known to those of skill in the art. Methods for measuring polarization density are also described hereinbelow.

DETAILED DESCRIPTION OF THE INVENTION

Figure 1D:
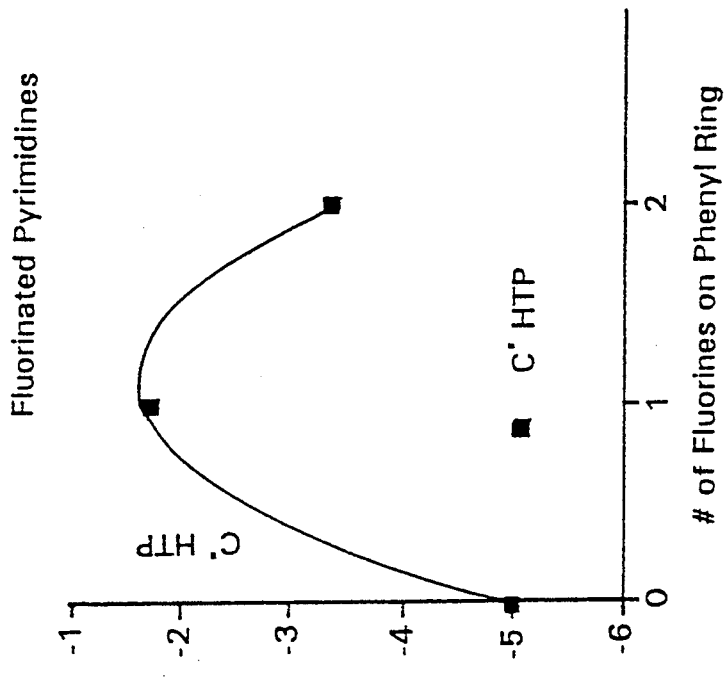
FIG. 1 contains graphs depicting the helical twisting power (HTP) of the compounds of Tables 3 and 4.

The compounds of the subject invention are synthesized by several methods, described hereinbelow, from a 4',4-substituted $R_1$—(Ar—Z)—OH compound, wherein Z represents either an ortho halide or meta and ortho halides on adjacent carbons on Ar. The 4',4-substituted $R_1$—(Ar—Z)—OH compounds are either commercially available, can be synthesized by known methods from readily available starting materials, or can be synthesized by routine modifications of methods described herein. For example, the synthesis of 4'-decyloxyphenyl-3-fluoro-4-hydroxybenzoate (X, where $R_1$=decyloxy and Z=ortho F) is described in the Examples.

In the Examples, the Ar employed are phenylbenzoate, phenylpyridine, phenylpyrimidine, diphenylpyridine, diphenylpyrimidine, etc.; however, as discussed hereinabove, any suitable FLC core can be employed in place of the exemplified cores, using methods known in the art or routine modifications of methods disclosed herein.

To synthesize a chiral 4'-$R_1$-phenyl-4-[(2,3-dihalo)alkoxy]-3-halobenzoate, a chiral 2,3-epoxy alkanol is coupled to the 4',4-substituted $R_1$—(Ar—Z)'OH compound; the epoxy ring is opened and treated with halogenating agents. Scheme 3 illustrates the synthesis of a 4'-$R_1$-phenyl-4-(2R,3R-dihalo)alkoxy-3-halobenzoate (XIV). As an example, the synthesis of 4'-decyloxyphenyl-4-[(2R,3R-difluoro)hexyloxy]-3-fluorobenzoate (XIV, where $R_1$=decyloxy, X, Y and Z=F, and $R_2$=propyl) follows Scheme 3 and is discussed in Example 3a.

To synthesize the enantiomer of the 4'-$R_1$-phenyl-4-[(2R,3R-dihalo)alkoxy]-3-halobenzoate (XIV) produced by the method Example 2a, the method of Example 2a is followed with the exception that the (2S,3S-epoxy)hexanol (XI, where $R_2$= propyl) is replaced with its enantiomer, (2R,3R-epoxy)hexanol.

The syntheses of the diastereomers of the 4'-$R_1$-phenyl-4-(2R,3R-dihalo)alkoxy-3-halobenzoate (XIV) produced by the method of Example 2a, can be accomplished by methods known to those of skill in the art from readily available materials, or as illustrated in the Examples below, i.e, the synthesis of 4'-decyloxyphenyl-4-[(2R,3S-difluoro)hexyloxy]-3-fluorobenzoate.

To synthesize 4'-$R_1$-phenyl-4-[(2S-halo)alkoxy]-3-halobenzoates (XVI), the method of Example 3a is followed. This method involves the coupling of 4'-$R_1$-phenyl-3-halo-4-hydroxybenzoate (X) with a chiral 2-haloalkanol. This method is exemplified by the synthesis of 4'-n-decyloxyphenyl-4-[(4-methyl-2S-fluoro)pentyloxy]-3-fluorobenzoate (XVI, where $R_1$=decyloxy, $R_2$=isopropyl, and X and Z=F) as discussed in Example 3a.

To synthesize the enantiomer of the 4'-$R_1$-phenyl-4-[(2S-halo)alkoxy]-3-halobenzoates (XVI) produced by the method of Example 3a, the method of Scheme 4 is followed with the exception that the enantiomer of the 2-haloalkanol used previously (XV) is substituted for the 2-haloalkanol.

To synthesize chiral 4'-$R_1$-phenyl-4-[(1-methyl-2-halo)alkoxy]-3-halobenzoates (XXII), the method of Example 4a is followed. This method involves the coupling of an epoxy alkanol to 4'-$R_1$-phenyl-3-halo-4- hydroxybenzoate (X), the opening of the epoxy ring and the treatment of the resulting hydroxy group with a halogenating agent. This method is illustrated in Scheme 6 and is exemplified by the synthesis of 4'-n-decyloxyphenyl-4-[(1S,4-dimethyl-2S-fluoro)pentyloxy]-3-fluorobenzoate (XXII, where $R_1$=decyloxy, $R_2$=isopropyl, and X and Z=F).

To obtain 4'-n-decyloxyphenyl-4-[(1R,4-dimethyl-2R-fluoro)pentyloxy]-3-fluorobenzoate, the enantiomer of 4'-n-decyloxyphenyl-4-[(1S,4-dimethyl-2S-fluoro)-pentyloxy]-3-fluorobenzoate, the procedure of Example 4a is followed with the exception that 1S,4-dimethyl-(2R,3R-epoxy)pentanol, the enantiomer of XIX ($R_2$=isopropyl), is used in place of compound XIX, as described in the Examples.

To obtain 4'-n-decyloxyphenyl-4-[(1R,4-dimethyl-2S-fluoro)pentyloxy]-3-fluorobenzoate, a diastereomer of 4'-n-decyloxyphenyl-4-[(1S,4-dimethyl-2S-fluoro)pentyloxy]-3-fluorobenzoate, the method of Example 4a is followed with the exception that a compound of formula XVII, a diastereomer of formula XIX, is used in place of the compound of formula XIX.

To synthesize the chiral 4'-$R_1$-phenyl-4-[(1-methyl-2,3-difluoro)alkoxy]-3-halobenzoates, the procedure of Example 5a as illustrated by Scheme 7 is followed. This method involves the coupling of an epoxy alkanol (compound of formula XIX) to 4'-$R_1$-phenyl-3-halo-4-hydroxybenzoate (X), the opening of the epoxy ring and the treatment of the resulting compound with a halogenating agent. This method is exemplified by the synthesis of 4'-decyloxyphenyl-4-[(1S,4-dimethyl-2R,3R-difluoro)pentanyloxy]-3-fluorobenzoate (MDW 205) (XXV, where $R_1$=decyloxy, X, Y and Z=F and $R_2$=isopropyl), described in the Examples.

To obtain 4'-decyloxyphenyl-4-[(1R,4-dimethyl-2S,3S-difluoro)pentanyloxy]-3-fluorobenzoate, the enantiomer of 4'-decyloxyphenyl-4-[(1S,4-dimethyl-2R,3R-difluoro)pentanyloxy]-3-fluorobenzoate (MDW 205) (Example 5a), the method of Example 5a is followed with the exception that 1S,4-dimethyl-(2R,3R-epoxy)pentanol is used in place of 1R,4-dimethyl-(2S,3S-epoxy)pentanol (XIX, where $R_2$=isopropyl).

The diastereomers of 4'-decyloxyphenyl-4-[(1S,4-dimethyl-2R,3R-difluoro)pentanyloxy]-3-fluorobenzoate (MDW 205) can be synthesized by known methods from readily available starting materials, as exemplified by the synthesis of 4'-decyloxyphenyl-4-[1R,4-dimethyl-2R,3R-difluoro)pentanyloxy]-3-fluorobenzoate (MDW235), as described in the Examples.

As is understood by those of skill in the art, the agents used in the methods described herein for opening the epoxy ring and for halogenating the resulting hydroxy group can be replaced by alternate agents to produce compositions in which X and/or Y=chloride or other halogens, or to produce compositions in which X is a different halide from Y. For example, opening the epoxy ring with HCl rather than (HF)$_x$·pyridine results in a chlorohydrin rather than a fluorohydrin; treating the resulting hydroxy group with a halogenating agent, DAST, produces a chlorofluoro alkoxy proximal segment. However, treating the hydroxy group with chlorinating agent produces a dichloro alkoxy proximal segment.

As is also understood by those of skill in the art, the 2-haloalkanol used to produce the 2-haloalkoxy chiral proximal segment of compound formula XVI can comprise any halide, but preferably fluorine or chlorine.

SCHEME 1:

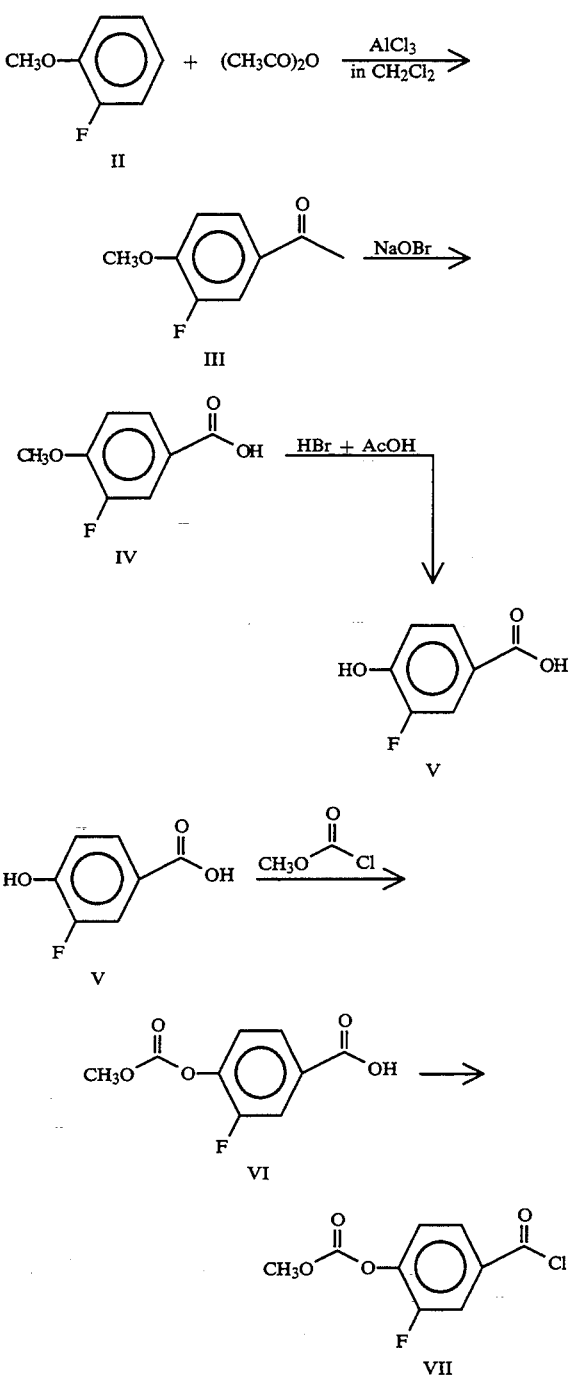

SCHEME 2:

-continued
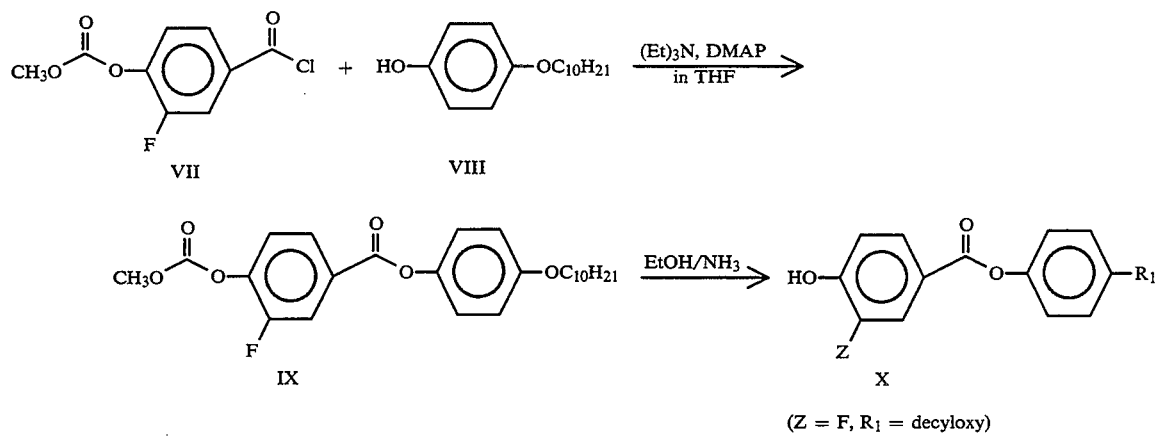
SCHEME 3:
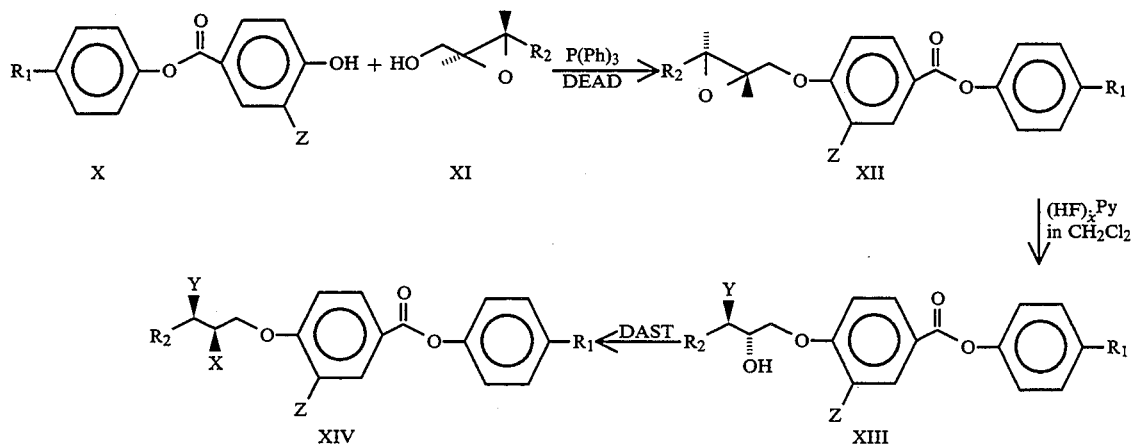
SCHEME 4:
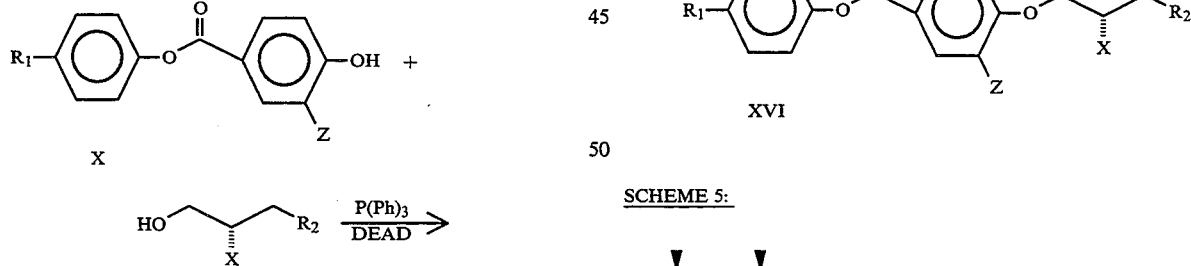
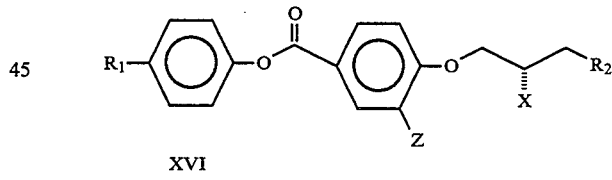
XVI
SCHEME 5:
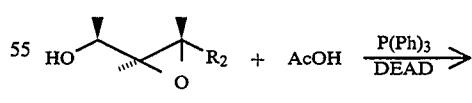
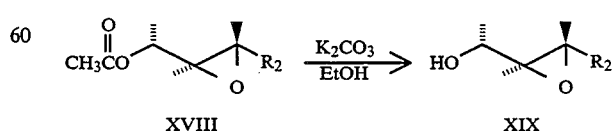
SCHEME 6:

-continued

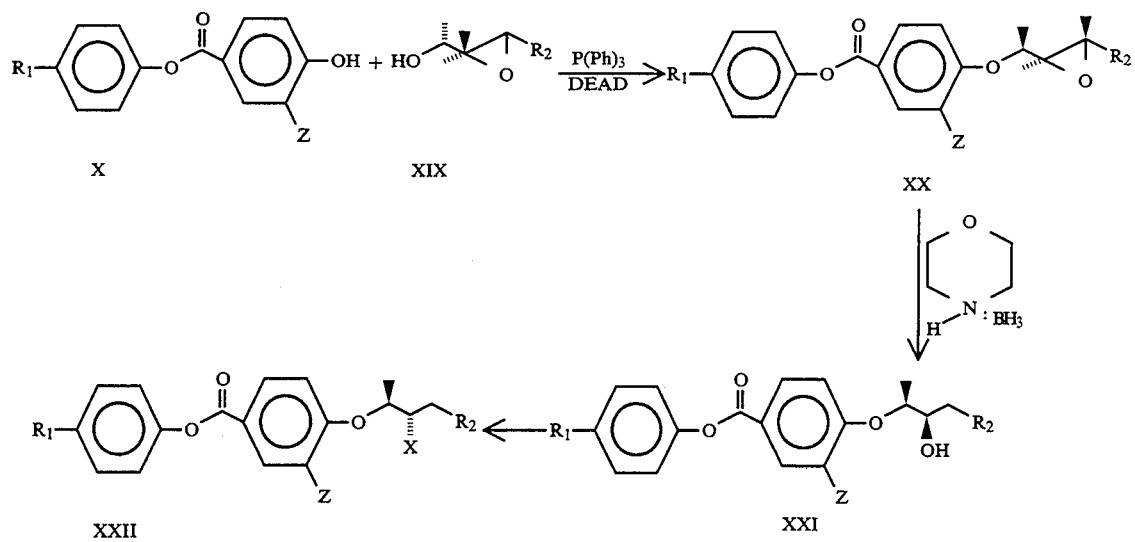

SCHEME 7:

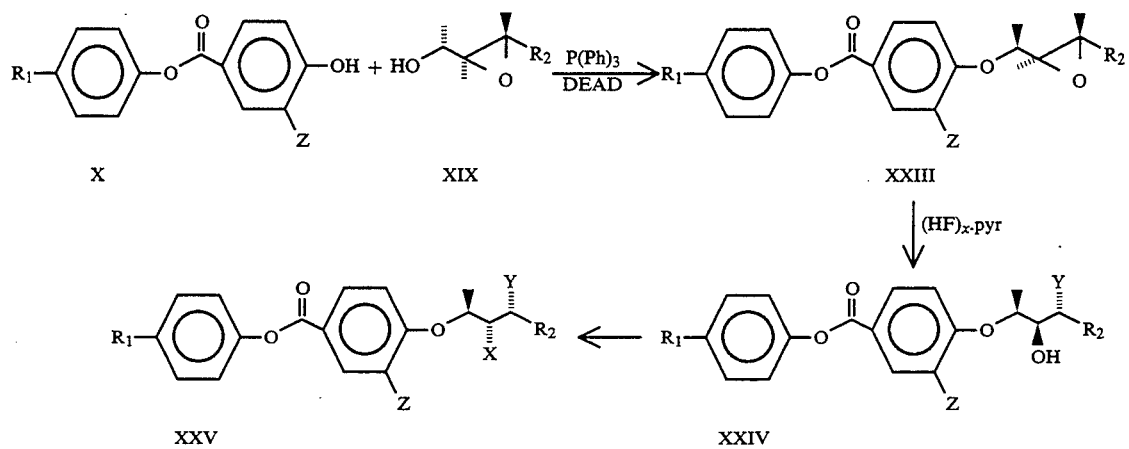

Many of the compounds of the subject invention, including compounds 4'-decyloxy-4-[(2S-fluoro-4-methyl)pentyloxy]-3-fluorobenzoate (general formula XVI), 4'-decyloxy-4-[(1S,4-dimethyl-2S-fluoro)pentyloxy]-3-fluorobenzoate (general formula XXII), 4'-decyloxy-4-[(2R,3R-difluoro)hexyloxy]-3-fluorobenzoate (general formula XIV), and 4'-decyloxy-4-[(1S,4-dimethyl-2R,3R-difluoro)pentyloxy]-3-fluorobenzoate (general formula XXV) of Table 2, do not possess an enantiotropic or monotropic ferroelectric (smectic C*) liquid crystal phase. However, when these compounds are mixed with a known FLC host material, such as W82, mixtures are produced which possess ferroelectric smectic C* phases and improved polarization density relative to that of the host material alone.

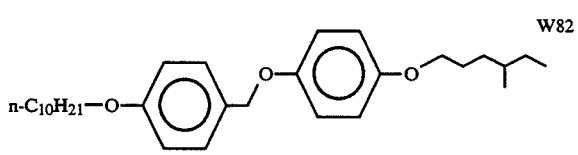

W82

Table 2 summarizes the polarization density and phase sequence temperatures of 10% (w/w) mixtures of subject compositions with W82. In Table 2, the phases are noted as X=crystal, I=isotropic liquid, A=smectic A, C*=smectic C, F*=smectic F, N*=chiral nematic, and phase sequence temperatures are given in °C. Spontaneous polarization densities ($P_s$) are given in $nC/cm^2$ and the magnitude of $P_s$ was measured by integration of the dynamic current response on reversing the applied electric field, as described in Martinot-Lagarde (1976) J. Phys. 37, C-3, p.129 and Martinot-Lagarde (1977) J. Phys. Lett. 38, L-17. $P_{s(ext)}$ is the polarization density for the subject compositions as extrapolated from a 10% by weight mixture of a subject composition in W82.

W82 is known to possess an enantiotropic ferroelectric C* phase with very low polarization density of about $-1$ $nC/cm^2$. Mixtures of the compounds of the present invention, particularly compounds as shown in Table 2, possess ferroelectric C* phases with higher polarization densities than W82 alone.

Compositions of the subject invention can also be mixed with host materials in any desired weight percentage. Generally, as the weight percentage of subject compositions in the host material is increased, polarization density of the FLC mixture increases linearly. Depending on the intended application, a person of skill in the art can determine the desired polarization of the FLC mixture and calculate the appropriate concentration of subject compositions in a host material to obtain the desired polarization in the mixture. Because the polarization densities of the subject compounds can be high, low concentrations are typically used as dopants to obtain the desired polarization in the mixture. Generally, the concentrations of the dopants used in the host are less than about 20% (w/w). Such low concentrations avoid orientational viscosity that may be associated with the use of higher concentrations of such dopants.

Generally, as dopant concentration in FLC mixture increases, the phase diagram of the mixture and the pitch may be altered. However, a person of skill in the art would be able to compensate for these effects. Further, compounds useful in pitch compensation are discussed herein.

Compositions of the subject invention can be mixed with any suitable host material. Suitable host materials vary with the intended application, but generally, solubility or miscibility with the dopant, broad C* phase temperature range (e.g., −20° C. to 60° C.) and low orientational viscosity are considered desirable for bistable SSFLC and DHF applications.

The polarization densities of FLC mixtures comprising the subject dopants can be greater than that of mixtures comprising analogous dopants not having a halogenated core and halogenated chiral tail, such as 4-decyloxyphenyl-4'-(1-methylhexyloxy)-benzoate. More specifically, 4-decyloxyphenyl-4'-(1-methylhexyloxy)-benzoate has a $P_{S(ext)}$ of −42 nC/cm$^2$. As can be seen from Table 2, each of the exemplified compositions has a $P_{S(ext)}$ equal to or greater than that of 4-decyloxyphenyl-4'-(1-methylhexyloxy)-benzoate.

Table 2 also includes polarization, tilt angle and phase sequence data for compounds analogous to compositions of the subject invention, i.e., compounds not having halide(s) on the core. As can be seen from Table 2, the addition of a halide to the aromatic ring of the core adjacent to the chiral tail can improve the polarization density. It is believed that this improved polarization density of the subject compositions can be due in some cases to the relative alignment of the individual dipole moments of the halide bond(s) on the core with the dipoles of the oxygen and halide bond(s) on the proximal segment of the chiral tail. More specifically, the dipoles of the core halide bond(s) and the proximal segment oxygen and halide bond(s) are believed in some of the subject compositions to be in relative alignment with each other and substantially normal to the tilt plane in an FLC mixture C* phase.

TABLE 2

Phase sequence polarization and tilt angle data for C* mixtures using W82 as a host and containing 10% (w/w) of subject compositions.

| | Phase Sequence °C. | $P_S$ | Tilt Θ | $P_{S(ext)}$ | $P_{S(ext)} \div \sin Θ$ |
|---|---|---|---|---|---|
| MDW 186 4'-decyloxyphenyl-4-(2-fluoro-4-methyl)pentyloxybenzoate | I $\xrightarrow{73.3}$ N* $\xrightarrow{72.3}$ A $\xrightarrow{68}$ C* $\xrightarrow{28}$ X | −2.29 | 25 | −14 | −33 |
| MDW 187 (XVI) 4'-decyloxyphenyl-4-[(2S-fluoro-4-methyl)pentyloxy]3-fluorobenzoate | I $\xrightarrow{71.5}$ N* $\xrightarrow{70.5}$ A $\xrightarrow{68.1}$ C* $\xrightarrow{26}$ X | −5.06 | 28 | −42 | −89 |
| MDW 215 4'-decyloxyphenyl-4-(1,4-dimethyl-2-fluoro)pentyloxybenzoate | I $\xrightarrow{64.6}$ A $\xrightarrow{75.3}$ C* $\xrightarrow{}$ X | −8.39 | 25 | −75 | −177 |
| MDW 225 4'-decyloxyphenyl-4-[(1S,4-dimethyl-2S-fluoro)pentyloxy]-3-fluorobenzoate | I $\xrightarrow{61.5}$ A $\xrightarrow{55.2}$ C* $\xrightarrow{24.3}$ X | −9.85 | 29.5 | −90 | −183 |
| MDW 190 4'-decyloxyphenyl-4-(2,3-difluoro)hexyloxybenzoate | I $\xrightarrow{71.4}$ A $\xrightarrow{66.2}$ C* $\xrightarrow{33.5}$ X | −3.83 | 26.5 | −29 | −56 |
| MDW 199 (XIV) 4'-decyloxyphenyl-4-[(2R,3R-difluoro)hexyloxy]-3-fluorobenzoate | I $\xrightarrow{71.5}$ A $\xrightarrow{67.5}$ C* $\xrightarrow{24.5}$ X | −12.11 | 27.5 | −112 | −243 |
| MDW 194 4'-decyloxyphenyl-4-(1,4-dimethyl-2,3-difluoro)pentyloxybenzoate | I $\xrightarrow{65.9}$ A $\xrightarrow{57.4}$ C* $\xrightarrow{18.3}$ F* $\xrightarrow{-2}$ X | −2.20 | 29.5 | −13 | −26 |

TABLE 2-continued

Phase sequence polarization and tilt angle data for C* mixtures using W82 as a host and containing 10% (w/w) of subject compositions.

| | Phase Sequence °C. | $P_s$ | Tilt $\Theta$ | $P_{s(ext)}$ | $P_{s(ext)} \div \sin \Theta$ |
|---|---|---|---|---|---|
| MDW 205 (XXV) 4'-decyloxyphenyl-4-[(1R,4-dimethyl-2R,3R-difluoro)pentyloxy]-3-fluorobenzoate | I $\xrightarrow{65.8}$ A $\xrightarrow{57.6}$ C* $\xrightarrow{18.2}$ F* $\xrightarrow{-2}$ X | −7.66 | 29.0 | −68 | −140 |

As indicated hereinabove, compositions of the subject invention containing the following proximal segments are preferred:

| | |
|---|---|
| 2S-halo | 2R-halo |
| 1S-methyl-2S-halo | 1R-methyl-2R-halo |
| 2S,3S-dihalo | 2R,3R-dihalo |
| 1S-methyl-2R,3R-dihalo | 1R-methyl-2S,3S-dihalo. |

Compositions containing these proximal segments are preferred because they can have polarization densities greater than their diastereomers. For example, subject compositions comprising 1S-methyl-2S-halo or 1R-methyl-2R-halo proximal segments have polarization densities greater than their diastereomers having either 1R-methyl-2S-halo or 1S-methyl-2R-halo proximal segments. Subject compositions comprising 2S,3S-dihalo or 2R,3R-dihalo proximal segments have polarization densities greater than their diastereomers having either 2R,3S-dihalo or 2S,3R-dihalo proximal segments. Finally, subject compositions comprising 1S-methyl-2R,3R-dihalo or 1R-methyl-2S,3S-dihalo proximal segments have polarization densities greater than their diastereomers having 1R-methyl-2R,3R-dihalo, 1S-methyl-2S,3S-dihalo, 1S-methyl-2S,3R-dihalo, 1R-methyl-2R,3S-dihalo, 1S-methyl-2R,3S-dihalo, or 1R-methyl-2S,3R-dihalo proximal segments.

It is believed that the subject compositions comprising the preferred proximal segments have greater polarization densities relative to their respective diastereomers due to the relative alignment of the dipole moments of the core halide(s) and the oxygen and halide(s) of the proximal segment in the preferred compositions. The dipoles of the core halide(s) and oxygen and halide(s) of the proximal segment are believed to be in relative alignment and substantially normal to the tilt plane in an FLC composition smectic C* phase.

It should be noted that it is dipole orientation of the subject conformations in the oriented smectic C phase that affects polarization density. Only the components of the dipoles normal to the tilt plane affect polarization. The structure of the proximal and distal segments of the achiral tail and steric interaction between the groups will affect dipole orientation and the magnitude and sign of the polarization density. The relationship between dipole alignment and ferroelectric polarization density has been discussed for related molecules in Walba et al. (1986) J. Amer. Chem. Soc. 108:5210–5221 and Walba et al. (1986) J. Amer. Chem. Soc. 108:7424–7425, both of which are incorporated herein in their entirety by reference.

The subject invention further comprises a method for distinguishing the compositions comprising the preferred proximal segments from their respective diastereomers. This method is based on the greater polarization density of a preferred composition relative to its diastereomers. For example, a sample of 4-decyloxyphenyl-4'-[(1S,4-dimethyl-2R,3R-difluoro)pentyloxy]-3-fluorobenzoate can be distinguished from a sample of 4-decyloxyphenyl-4'-[(1R,4-dimethyl-2R,3R-difluoro)pentyloxy]-3-fluorobenzoate by the greater polarization density of the former.

The method for distinguishing a preferred composition from one of its diastereomers comprises the steps of:

(a) measuring the polarization density of samples of each isomer, and (b) selecting the composition having the greatest polarization density.

The isomer having the larger polarization density is the composition having the preferred proximal segment.

It is believed that the composition selected by this selection method has a greater polarization density because the dipole moments of its core halide(s) and proximal segment oxygen and halide(s) bonds are relatively aligned substantially normal to the tilt plane in an FLC composition smectic C* phase. For example, 4-decyloxyphenyl-4'-[(1S,4-dimethyl-2R,3R-difluoro)pentyloxy]3-fluorobenzoate has a greater polarization density than its diastereomer, 4-decyloxyphenyl-4'-[(1R,4-dimethyl-2R,3R-difluoro)pentyloxy]-3-fluorobenzoate, due to the relative alignment of the dipoles of the core fluoride and proximal segment oxygen and fluorides.

The subject invention also comprises a method for selecting subject compositions having an absolute polarization density greater than about 1 nC/cm$^2$. As used herein "absolute polarization density greater than about 1 nC/cm$^2$" means a polarization density having a positive numerical value greater than about +1 nC/cm$^2$ or a negative numerical greater than about −1 nC/cm$^2$, e.g., −5 nC/cm$^2$.

The method for selecting subject compositions having an absolute polarization density greater than about 1 nC/cm$^2$ comprises the steps:

(a) synthesizing subject compositions comprising an ortho or ortho and meta halogenated core and a 1-methyl-2-haloalkoxy, 2-haloalkoxy, 2,3-haloalkoxy or 1-methyl-2,3-dihaloalkoxy proximal segment by methods described herein, (b) measuring the polarization densities of the compositions synthesized in (a) by methods described herein, (c) selecting from the compositions of step (b) those compositions having an absolute polarization density greater than about 1 nC/cm$^2$.

As described herein, because many of the subject compositions in pure form do not have a smectic C* phase, the polarization density of a particular composition can be assigned by extrapolating the polarization value of an FLC mixture, e.g., a 10% by weight mixture of the dopant in W82, to a theoretical polarization value based on a 100% dopant composition and an assumed C* phase for the dopant. The terms "absolute polarization density" and "polarization density" are meant to include such extrapolated polarizations.

As described herein, some compounds of the present invention have properties other than or in addition to improved polarization density and fast switching speed, which make them useful in bistable SSFLC applications or in DHF applications. For example, subject FLC compounds having a phenylpyrimidine or phenylpyridine core with either ortho or ortho and meta fluorination (and their phase diagrams, $P_s$, $\tau$, $\Theta$, and pitch) are presented in Tables 3 and 4. Table 3 shows data for the phenylpyrimidine series, including both the alkyl and alkoxy $R_1$s, and Table 4 shows data for the phenylpyridine series. Note that two different phenylpyrimidine hosts were used for these evaluations, but that one compound (MDW 232) was evaluated in both hosts to provide a standard for comparison.

smectic C* phase, and the majority of the compounds have no liquid crystalline phases whatsoever. In fact, with the exception of the monofluorinated phenylpyridine (which has a 3° monotropic A phase), only those compounds with an alkoxy achiral tail have mesomorphic phases. However, the lack of mesomorphism in these compounds does not inhibit their usefulness as FLC dopants. In fact, when placed into a host mixture they do not greatly alter the mixture's phase diagrams, as can be seen from the data presented in Tables 3 and 4.

Thus, many of the difluoroalkoxy compounds only moderately (0°–5° C.) suppress the I→N, N→A, and A→C phase transition temperatures. However, certain of the compounds strongly suppressed one or more of the phase transitions. It was found that the compounds with one fluorine on the core suppressed the A→C

TABLE 3

Difluoroalkoxy dopants at 10% concentration in phenylpyrimidine host MX6033[a]

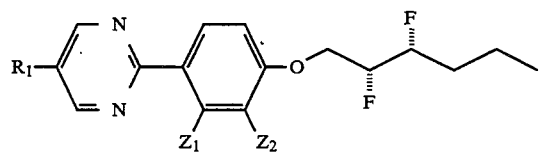

| ID# | $R_1$ | $Z_1$, $Z_2$ | SmC—SmA—Ch—I | | | $P_s$ (nC/cm$^2$) | $\theta$(°) | $P_o$[b] | 10-90 ($\mu$s)[c] | N*pitch ($\mu$m) | C*pitch ($\mu$m) |
|---|---|---|---|---|---|---|---|---|---|---|---|
| MDW232 | $C_8H_{17}-$ | H, H | 60 | 72 | 81 | −23.5 | 27.5 | −510 | 59 | −7 | −2 |
| MDW432 | $C_8H_{17}-$ | H, F | 54 | 74 | 81 | −15.0 | 21.5 | −410 | 120 | +16 | −6 |
| MDW434 | $C_8H_{17}-$ | F, F | 61 | 70 | 80 | −18.3 | 26.5 | −410 | 60 | +3 | −3 |
| MDW428 | $C_8H_{17}O-$ | H, H | 61 | 73 | 86 | −13.7 | 25.0 | −320 | 72 | −4 | −3 |
| MDW427 | $C_8H_{17}O-$ | H, F | 54 | 79 | 85 | −8.9 | 22.5 | −230 | 105 | −4 | −6 |
| MDW433 | $C_8H_{17}O-$ | F, F | — | — | — | −12.7 | 26 | −290 | 84 | +7.1 | −3 |

[a]MX6033 host phase diagram, $S_C$-63—>$S_A$—>N-85—>I.
[b]$P_o$ was obtained by multiplying $P_s$ by 10 to give $P_{ext}$ and dividing by sin $\theta$.
[c]Rise time measurement performed in 1.7 $\mu$m cell at 5V/$\mu$m, at T = 22° C.

TABLE 4

Difluoroalkoxy dopants at 10% concentration in phenylpyrimidine host MX6396[a]

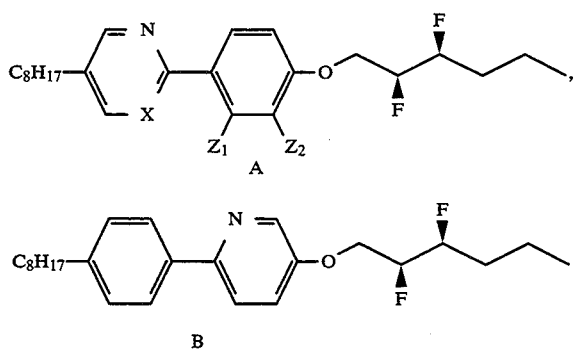

| ID# | TYPE | X, $Z_1$, $Z_2$ | X "SmC | "SmA | "Ch | "I | $P_s$[d] nC/cm$^2$ | $\Theta$ | $P_o$[b] | $\tau_{10-90}$ $\mu$s[c,d] | N*pitch[e] $\mu$m(°C.) | C*pitch[e] $\mu$m |
|---|---|---|---|---|---|---|---|---|---|---|---|---|
| MDW232 | A | N, H, H | −1.1 | 64 | 78 | 86 | −25.3 | 24 | −620 | 55 | −5(80) | −0.8 |
| MDW299 | A | C, H, H | −0.4 | 67 | 77 | 86 | −24.4 | 25 | −580 | 62 | −5(79) | −0.8 |
| MDW584 | A | C, H, F | −2.5 | 58 | 74 | 83 | −20.0 | 23 | −510 | 59 | −43(76) | −1.2 |
| MDW585 | A | C, F, F | −2.1 | 54 | 68 | 81 | −15.8 | 23 | −400 | 77 | +12(69) | −2 |
| MDW510 | B | — | −1.1 | 66 | 77 | 86 | −21.8 | 24 | −540 | 61 | −6(78) | −1.25 |

[a]MX6396 host phase diagram, X-0.8-$S_C$-67.5-$S_A$-81-N-89-I.
[b]$P_o$ was obtained by multiplying $P_s$ by 10 to give $P_{ext}$ and dividing by sin $\Theta$.
[c]Rise time measurements performed in 1.7 $\mu$m cell at 5V/$\mu$m.
[d]Measurements performed at 22° C.
[e]N* pitches all diverge; C* pitches all converge.

The phase diagrams of Tables 3 and 4 indicate that only the dialkoxyphenylpyrimidine, MDW 427, has a transition by approximately 9° C., and the compounds with two fluorines on the core suppressed the N→A transition by 7° C. or more. The monofluorinated and difluorinated phenylpyridines strongly suppressed all three phase transitions.

The measured polarization values for all dopants of Tables 3 and 4 were negative. This is consistent with the sign of polarization predicted by the Boulder model (Walba, D. M. et al. (1986) J. Am. Chem. Soc. 108:5210) for the 2R,3R-difluoroalkoxy tail. Fluorination of the core in all cases reduced the polarization. Replacement of the phenylpyrimidine's $R_1$ alkyl tail with an alkoxy tail reduced the polarization, but changing from a pyrimidine to a pyridine had minimal effect on the polarization.

A comparison of the properties of the compounds of Tables 3 and 4 with compounds having a phenylbenzoate core (Table 2) reveals that fluorination of the phenylbenzoate core significantly increases polarization. In contrast, fluorination of the phenylpyrimidine or phenylpyridine core decreases polarization. This indicates that in the phenylbenzoate system, the fluorinated ring is normal to the smectic C* layer tilt plane, thereby contributing to $P_s$. Ring orientation in the phenylpyrimidine system is less well understood, but ring fluorination helps probe the ring orientation. Since fluorination of the ring does not increase $P_s$, the fluorinated ring probably resides in the tilt plane, therefore not contributing to $P_s$. Indeed, the rings are not sterically driven to be orthogonal (from a calculation by Alchemy II™, from Tripos Associates), so it may be that the rings are coplanar, both in the tilt plane. Experimental error could account for the differences in $P_s$ between the phenylpyrimidine and phenylpyridine series, so the two systems apparently have similar ring orientations. However, the model of coplanar rings in the tilt plane does not explain either the 20% decrease in $P_s$ in both the mono- and difluorinated alkylpyridine and -pyrimidine cases or the further $P_s$ decrease in the alkoxy pyrimidine cases. It may be that the electronwithdrawing capabilities of the additional electronegative atoms reduce the C-O dipole moment of the chiral tail, or increase the likelihood of ring coplanarity.

The rise times of the compounds of Tables 3 and 4 vary from 55 to 120 μsec at 5V/μm. While some variation in rise time can be attributed to the differences in polarization and tilt angle, this does not fully account for the rise time variability, so there must also be differences in orientational viscosity. Preliminary assessment of the rise time data indicates that, at least in these systems, monofluorination results in higher viscosity than the unfluorinated system, whereas difluorination results in lower viscosity than the unfluorinated system. The phenylpyridine system appears to experience lower viscosity than the phenylpyrimidine system.

As discussed hereinabove, the N* and C* pitch are manifestations of the chirality of the liquid crystal material. In an SSFLC, both the N* and C* should be long to improve alignment in the FLC composition. Additionally, a long C* pitch avoids undesirable diffraction patterns and discontinuity lines in the cell. However, in DHF applications, tight C* pitch is desirable; additionally, compounds having reversed or lengthened N* pitch can be used as pitch compensating agents.

N* and C* pitch induction capability of compounds can be assessed by determining their helical twisting power (HTP), defined as the inverse of the induced pitch extrapolated to 100% concentration of the pitch inducer. The HTP of the compounds of Tables 3 and 4 are shown in FIGS. 1 and 2.

Figure 1C:
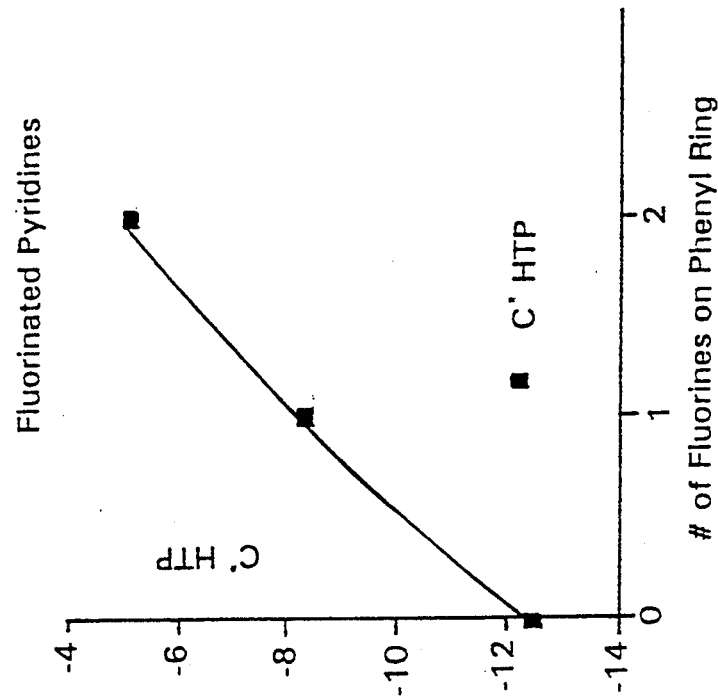

The top two graphs of FIG. 1 show the N* HTP, while the bottom two graphs show the C* HTP; the left two show the phenylpyridine system, while the right two show the phenylpyrimidine system. It can be seen that the number of fluorines on the aromatic core can profoundly affect both the C* and the N* HTP of a material. In the N* phase, the HTP is small, but has the largest magnitude for the non-fluorinated compounds. In the C* phase, the unfluorinated compounds also have the largest magnitude HTP. For the pyridines, the monofluorinated compound has a stronger C* HTP than the difluorinated compound, while the reverse is true for the phenylpyrimidines. Note that in both the phenylpyridines and the phenylpyrimidines, the N* HTP is very small (i.e., the N* pitch is very long) for the monofluorinated compound and the sign reverses for the difluorinated compound. This makes both the mono- and difluorinated compounds ideal for DHF applications, presenting the possibility of mixtures of difluoroalkoxy compounds with are self-pitch compensated in the N* phase.

Figure 2B:
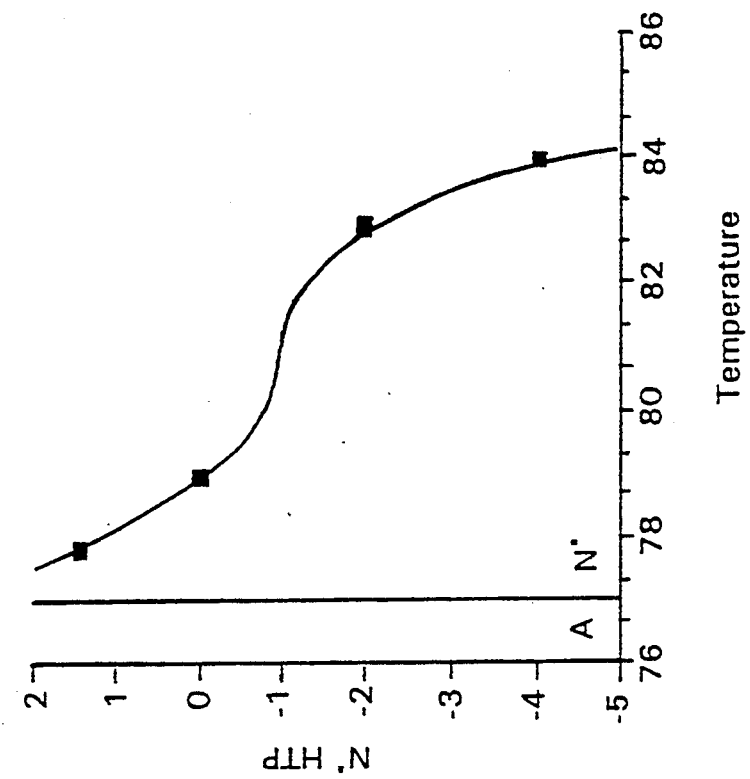
FIG. 2 contains graphs illustrating the anomalous N* HTP behavior of the compounds of Tables 3 and 4.
Figure 2A:
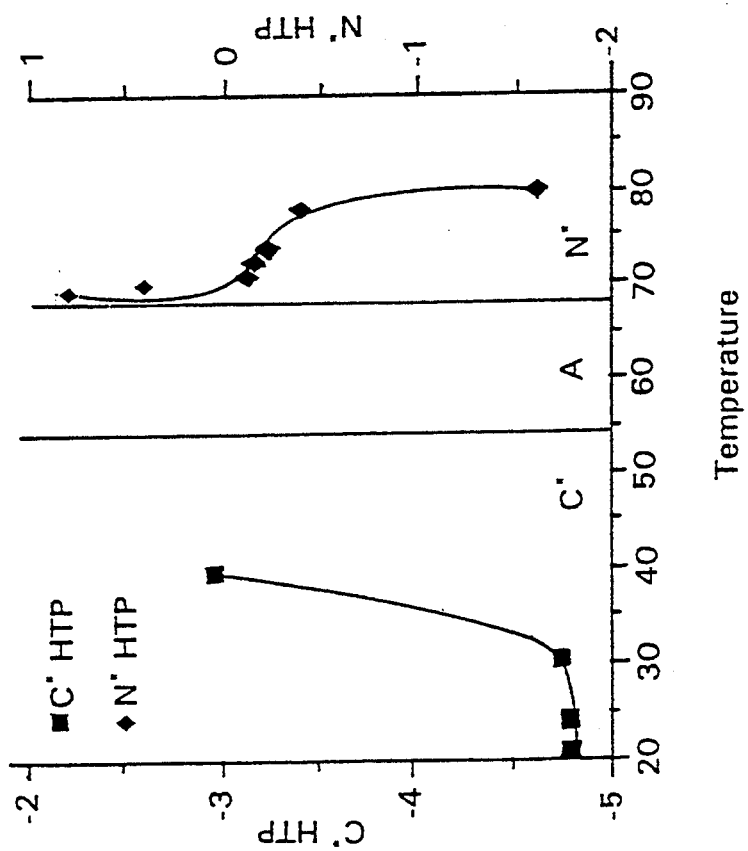

The core-difluorinated phenylpyridine and phenylpyrimidine both showed anomalous N* HTP behavior, as is shown in FIG. 2. At higher temperatures, they had strong negative N* HTP, but when the temperature decreased the N* pitch was unwound to infinity. Then as the temperature continued to decrease, the N* helix rewound in the positive direction, giving a relatively stong positive N* HTP as the material reached the N→A transition temperature.

In the subject invention, compounds of the formula

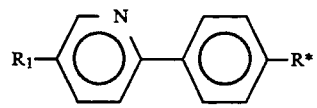

wherein Z is a ortho halide, $R_1$ is an alkoxy group, Ar, without limitation, can be any of the cores of Table 5 (where R* symbolizes the chiral tail), and the chiral proximal segment is 2R, 3R- or 2S, 3S-dihaloalkoxy, demonstrate elongated C* pitch. See, e.g., compound MDW 427 in Table 3, which has an elongated C* pitch without a decrease in N* pitch relative to the unhalogenated core analog. These properties make this group of compounds useful in SSFLC applications, where both the N* and C* should be long.

TABLE 5

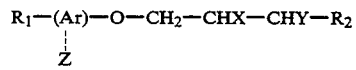 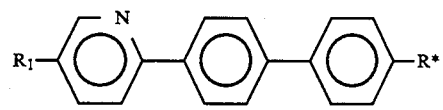

TABLE 5-continued

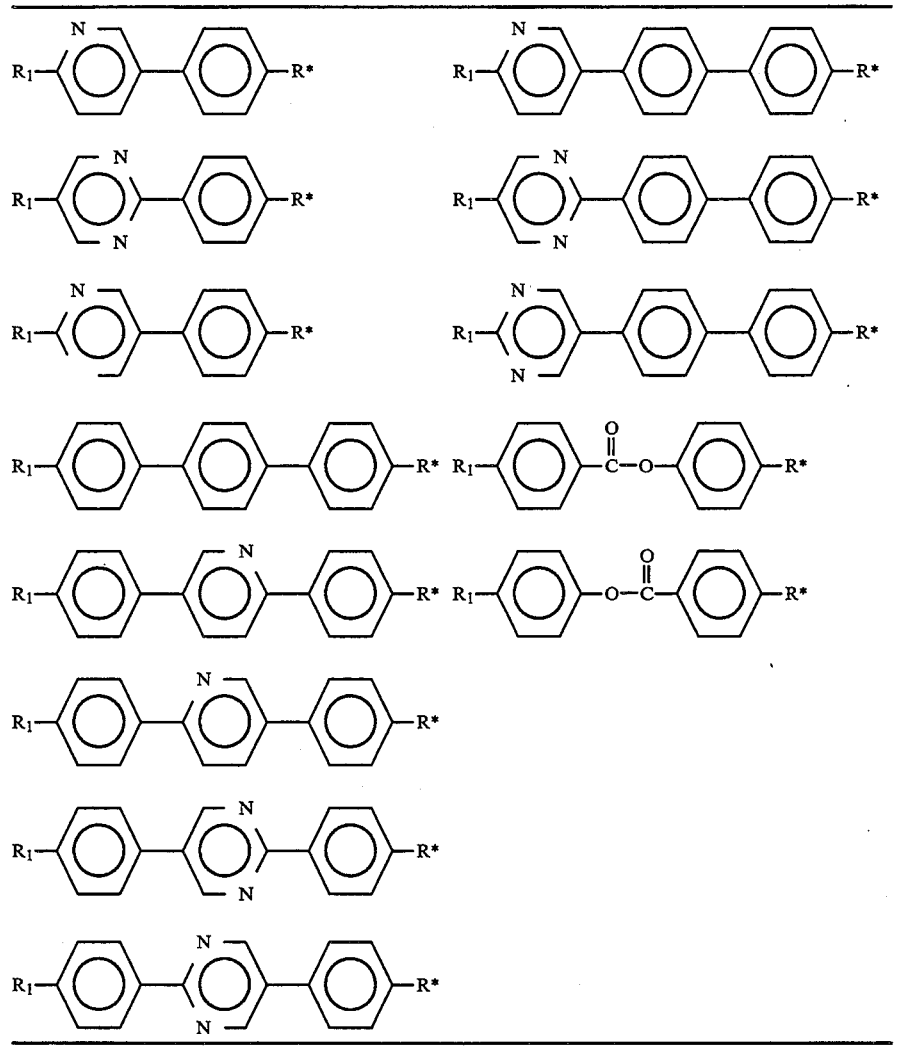

Additionally, compounds of the formula

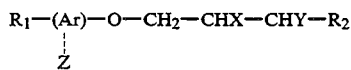

wherein Z is both ortho and meta halides, R₁ is alkyl, alkenyl or alkoxy, Ar can be (without limitation) any of the cores of Table 6, and the chiral proximal segment is 2R,3R- or 2S,3S-dihaloalkoxy, demonstrate inverted or lengthened N* pitch while maintaining a tight C* pitch relative to their non-halogenated core analogs. Table 3 provides a comparison of difluorinated core compounds MDW 434 and 433 to their corresponding non-fluorinated core analogs, MDW 232 and MDW428, respectively. Table 3 shows that when the core is ortho and meta halogenated, N* pitch is reversed regardless of whether R₁ is alkoxy or alkyl. Additionally, the rise times of MDW434 and MDW433 are comparable to those of MDW232 and MDW428, respectively, indicating that switching speed may not be compromised. Because these compounds have reversed N* pitch without substantial change in their C* pitch relative to their non-halogenated core analogs, they are useful as N* pitch compensating agents in DHF applications.

TABLE 6

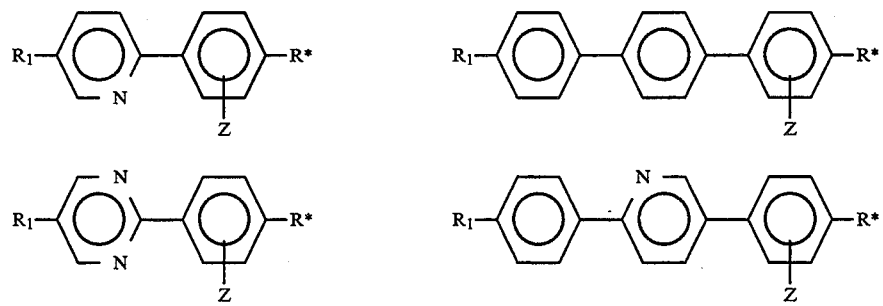

TABLE 6-continued

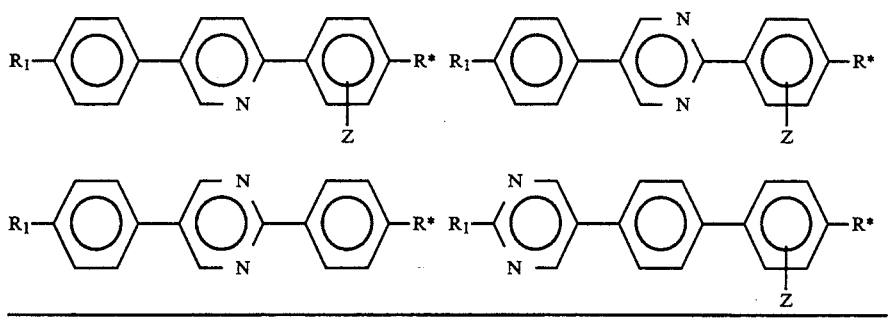

Table 7 provides N* and C* pitch values of difluorinated core compounds MDW 649 and MDW 655. Both these three ring compounds show longer N* pitch than their respective non-fluorinated core analogs while retaining tight C* pitch. The longer N* pitch in combination with tight C* pitch makes these compounds useful as N* pitch compensating agents in DHF applications.

diagram, and N* and C* pitches for subject compound MDW652. MDW652 is useful in SSFLC applications as an N* and C* pitch compensating agent.

TABLE 8

MDW652

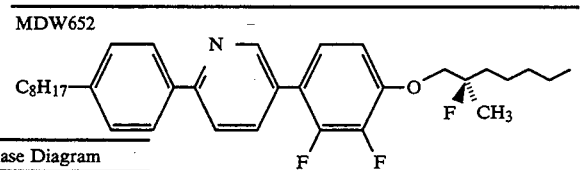

TABLE 7

| Host[1] | Dopant | N* Pitch[2] | C* Pitch[3] | $P_s{}^3$ | Phase Diagram |
|---------|--------|-------------|-------------|-----------|---------------|
| MX6033 | MDW232 | −7 | −2 | −24 | I-81-N*-72-A-61-C* |
| MX6396 | MDW232 | −3 | −1 | −25 | I-86-N*-78-A-65-C* |
| MX6033 | MDW299 | −2.6 | | −25 | I-85-N*-74-A-64-C* |
| MX6396 | MDW299 | −2 | −1.2 | −24 | I-86-N*-78-A-68-C* |
| MX6033 | MDW655 | −37 | −2 | −8 | I-91-N*-84-A-67-C* |
| MX6396 | MDW649 | −9 | −2 | −16 | I-91-N*-80-A-72-C* |

[1]Host phase diagrams are described in Tables 3 and 4. Concentration of dopan in host was 10% (w/w) in each case.
[2]N* was measured at 2° above N*-A transition.
[3]Measured at 22° C.

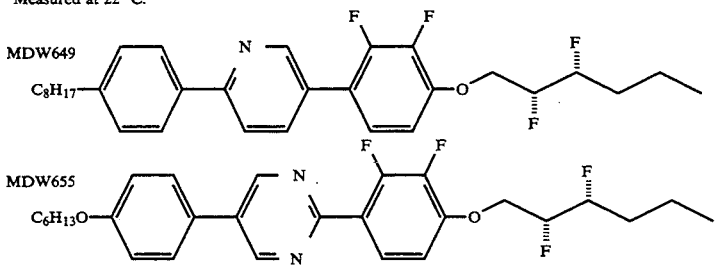

Additionally, compounds of the formula

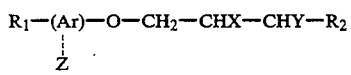

wherein Z is an ortho halide, R₁ is alkyl or alkenyl, Ar is any of the cores of Table 5, and the chiral proximal segment is 2R,3R- or 2S,3S-dihaloalkoxy, can have a long N* and short C* pitch, making them useful in DHF applications.

Further, compounds of the formula:

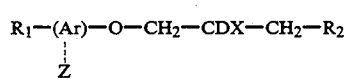

wherein Z is both ortho and meta halides, R₁ is alkyl, alkenyl or alkoxy, Ar is any of the cores of Table 1, and the chiral proximal segment is 2R- or 2S-methyl-2-haloalkoxy, can also have $P_s$, N* pitch, or C* pitch that makes the compounds useful in DHF or SSFLC applications. For example, Table 8 indicates the $P_s$, phase

| Host[1] | N* Pitch[2] | C* Pitch[3] | $P_s{}^4$ | Phase Diagram |
|---------|-------------|-------------|-----------|---------------|
| MX6111 | 2.55 | 2.2 | −3.4 | I-78-N-73-A-65-C-<RT-X |

[1]10% MDW652 in MX6111. Phase diagram for MX6111 is: I-78-N-70-A-57-C*.
[2]μm, measured at 75° C.
[3]μm, measured at 21° C.
[4]Measured at 21° C., at 6 V/μm field, in nC/cm².

EXAMPLES

Example 1 Synthesis of 4'-R₁-phenyl-3-halo-4-hydroxy benzoates (X)

This example illustrates the synthesis of 4'-R₁-phenyl-3-halo-4-hydroxy benzoates, which can be used in the remaining Examples to produce phenyl halobenzoates having the chiral tails of the subject invention. The synthesis of 4'-R₁-phenyl-3-halo-4-hydroxy benzoates is illustrated by the synthesis of 4'-decyloxyphenyl-3-fluoro-4-hydroxybenzoate (X, where R₁=decyloxy and Z=F) described hereinbelow and illustrated in Schemes 1 and 2.

Initially, 2-fluoroanisole (II) was used to synthesize 3-fluoro-4-methoxyacetophenone (III). AlCl$_3$ (0.6 mol) and acetic anhydride (0.4 mol) were placed in 250 ml of dry dicloromethane. The 2-fluoroanisol (0.2 mol) was added dropwise over a period of 30 minutes to the reaction mixture which was then stirred with a magnetic stir bar for two hours. The reaction was judged complete by TLC. The reaction mixture was then poured in ice and stirred for one hour. The CH$_2$Cl$_2$ layer was separated and the water layer was extracted twice with CH$_2$Cl$_2$. Organic layers were combined and washed with 3N HCl and water, dried with MgSO$_4$ and passed through a thick pad of silica. The solvent was rotary evaporated to obtain the crude product, which was crystallized from 7% (v/v) ethyl acetate in hexanes to obtain 70% yield of the crystallized product, 3-fluoro-4-methoxyacetophenone (III).

3-fluoro-4-methoxyacetophenone (11.5 g) was dissolved in 100 ml dioxane and NaOBr solution (as prepared below) was added dropwise, with constant stirring with a stir bar at room temperature. The NaOBr solution was prepared by dissolving 40 g of NaOH in 500 ml of water, cooling to 0° C. in an ice bath, and adding bromine (12.5 ml) dropwise while stirring with stir bar; bromine was added slowly so that the reaction mixture did not exceed 5° C. After overnight stirring of the 3-fluoro-4-methoxyacetophenone, dioxane and NaOBr solution, the reaction mixture was diluted with water (200 ml). Since the reaction mixture was basic, the product, benzoic acid, was in water as its sodium salt. The resultant mixture was partitioned between ether and water. The ether layer was washed with dilute aqueous NaOH to extract any remaining product as Na salt. The aqueous layers were combined and acidified to pH 1 to precipitate the benzoic acid. The resulting acid was extracted with ether. The ether layer was washed with water a few times, dried with MgSO$_4$, and filtered. Rotary evaporation of the ether fraction afforded 3-fluoro-4-methoxybenzoic acid (IV) in 85% yield.

Next, the 3-fluoro-4-methoxybenzoic acid (IV) was digested with HBr (20 ml) and glacial acetic acid (40 ml) overnight. Most of the acetic acid was distilled off and the remaining mixture was diluted with water. The precipitated benzoic acid was extracted in ether; the ether layer was dried, filtered and rotary evaporated to produce 11.0 g of the 3-fluoro-4-hydroxybenzoic acid (V).

4-methoxycarbonyloxy-3-fluorobenzoic acid (VI) was synthesized from 3-fluoro-4-hydroxybenzoic acid (V) by reaction of the latter with methyl chloroformate. NaOH (90 mmol) and 3-fluoro-4-hydroxybenzoic acid (30 mmol) were dissolved in water (80 ml) and cooled to −20° C. Methyl chloroformate (45 mmol) was added dropwise to the mixture. The mixture was then stirred with a magnetic stir bar at 5° C. for four hours and left overnight in the refrigerator. The mixture was then acidified to pH 5 to precipitate 4-methoxycarbonyloxy-3-fluorobenzoic acid. The precipitates were filtered and crystallized from acetonitrile to afford the clean product, 4-methoxycarbonyloxy-3-fluorobenzoic acid (VI), in a 77% yield.

To produce 4-methoxycarbonyloxy-3-fluorobenzoyl chloride (VII), the 4-methoxycarbonyloxy-3-fluorobenzoic acid (VI) (2.4 mmol) was refluxed overnight in neat oxalylchloride; excess oxalylchloride was removed under vacuum and traces of it were removed under high vacuum. The 4-methoxycarbonloxy-3-fluorobenzoyl chloride (2.4 mmol) (VII) and 4-decyloxyphenol (VIII) (2.4 mmol) were dissolved in dry cold (0° C.) THF. Triethylamine (8 mmol) was added dropwise, followed by a catalytic amount of DMAP. The reaction mixture was then stirred with a magnetic stir bar for three hours at room temperature. The solvent was then rotary evaporated until dryness and the residue was passed through a thick pad of silica using 20% (v/v) hexanes in CH$_2$Cl$_2$. The solvent was taken off under vacuum to obtain the produce, 4'-n-decyloxyphenyl-4-methoxycarbonyloxy-3-fluorobenzoate (IX), in 80% yield.

1.92 mmol of the 4'-n-decyloxyphenyl-4-methoxycarbonyloxy-3-fluorobenzoate (IX) was dissolved in 50 ml of ethanol and 2 ml of aqueous 30% NH$_3$ (v/v) was added to it. The reaction mixture was stirred for 30 minutes with a magnetic stir bar. After the reaction was complete, the solution was poured into water and cooled in dry ice. The precipitate product was filtered and recrystallized from acetonitrile to afford 4'-decyloxyphenyl-(4-hydroxy-3-fluoro)benzoate (X, where R$_1$=decyloxy and Z=F) in 85% yield.

Example 1a Other 4'-R$_1$-4-hydroxy Substituted Cores Useful in Synthesis of Subject Compositions Other 4'-R$_1$,4-hydroxy substituted cores are either commercially available or can be synthesized by known methods from readily available starting materials. A variety of achiral tails, i.e., alkyl, alkenyl or alkoxy that are straight chain or branched, or have other variations as described hereinabove, can be appended by known meEhods to the core 4' relative to the 4-hydroxy substitution on the core. Further, cores having o-halo or o,m-dihalo substitution relative to the 4-hydroxy substitution are commercially available or can be synthesized by known methods from readily available starting materials. These other 4'-R$_1$,4-hydroxy substituted cores can be used in the methods of the remaining Examples.

Example 2 Synthesis of Chiral 4'-R$_1$-phenyl-4-[(2,3-dihalo)alkoxy]-3-halobenzoates (XIV)

This example illustrates the synthesis of nonracemic chiral 4'-R$_1$-phenyl-4-[(2,3-dihalo)alkoxy]-3-halobenzoates by stereospecific (or selective) halogenation of chiral phenylbenzoate epoxides. These syntheses proceed through 2,3 halohydrin intermediates. The procedure is illustrated by the synthesis of the trifluoride, 4'-n-decyloxyphenyl-4-[(2R,3R-difluoro)hexyloxy]-3-fluoro-benzoate (XIV, where R$_1$=decyloxy, X, Y and Z=F, and R$_2$=propyl).

Example 2a Synthesis of 4'-n-decyloxyphenyl-4-(2R,3R-difluoro)hexyloxy-3-fluoro-benzoate 2.1 mmol of 4'-decyloxyphenyl-4-hydroxy-3-fluorobenzoate (X, where R$_1$=decyloxy and Z=F), 2.3 mmol of (2S,3S-epoxy)hexanol (XI, where R$_2$=propyl), and 3 mmol of triphenylphosphine were dissolved in 10 ml of dry THF. A solution of diisopropyl azodicarboxylate (DEAD) (3 mmol) in 1 ml of dry THF was added dropwise over a period of two hours. The reaction mixture was stirred for two hours with a magnetic stir bar. The solvent was then taken off under vacuum and the residue was flash chromatographed (silica gel column) using 5% (v/v) ethyl acetate in hexanes as eluent to afford the (2S,3S) epoxy product, 4'-decyloxyphenyl-4-[(2S,3S-epoxy)hexyloxy]-3-fluorobenzoate (XII, where R$_1$=decyloxy, Z=F, R$_2$=propyl), in 44% yield.

120 mg of 4'-decyloxyphenyl-4-[(2S,3S-epoxy)hexyloxy]-3-fluorobenzoate was then dissolved in 10 ml of dry $CH_2Cl_2$ and cooled to 0° C. 0.5 ml of hydrogen fluoride in pyridine was added to the cold solution and stirred with a magnetic stir bar for one hour. The reaction was judged complete by TLC. The reaction was then quenched by the addition of cold water and stirring with a magnetic stir bar for 15 minutes. The solvent was rotary evaporated and the residue was flash chromatographed on a silica column using 10% (v/v) ethyl acetate in hexanes to obtain 72.8% yield of the fluorohydrin product, XIII where $R_1$=decyloxy, X and Z=F and $R_2$ =propyl.

In a flame dried argon filled flask, the fluorohydrin product (0.25 mmol) was dissolved in 20 ml of dry $CH_2Cl_2$ and cooled to −70° C. 0.1 ml of dimethylaminosulfurtrifluoride (DAST) was added to the reaction mixture and was allowed to stir with a magnetic stir bar for two hours at −70° C. The reaction mixture was stored in the refrigerator overnight. The reaction was quenched by addition of cold $NaHCO_3$ solution and stirring with a magnetic stir bar for 15 minutes. The product was extracted twice with 50 ml portions of $CH_2Cl_2$. Organic layers were combined and washed repeatedly with $NaHCO_3$ solution and brine, dried with $MgSO_4$, filtered and rotary evaporated. The residue was flash chromatographed on a silica column using 5% (v/v) ethyl acetate in hexanes to obtain 79% yield. The final product, 4'-decyloxyphenyl-4-[(2R,3R-difluoro)hexyloxy]-3-fluorobenzoate (XIV, where $R_1$=decyloxy, X, Y and Z=F, and $R_2$=propyl) was further purified by crystallization from hexanes.

Example 2b Synthesis of 4'-decyloxyphenyl-4-[(2S,3S-difluoro)hexyloxy]-3-fluorobenzoate The synthesis of 4'-decyloxyphenyl-4-[(2S,3S-difluoro)hexyloxy]-3-fluorobenzoate is accomplished by following the same method of Example 2a with the exception that (2R,3R-epoxy)hexanol is used in place of its enantiomer, (2S,3S-epoxy)hexanol (XI, where $R_2$=propyl).

Example 2c Synthesis of 4'-decyloxyphenyl-4-[(2R,3S-difluoro)hexyloxy]-3-fluorobenzoate The synthesis of 4'-decyloxyphenyl-4-[(2R,3S-difluoro)hexyloxy]-3-fluorobenzoate, the diastereomer of 4'-decyloxyphenyl-4-[(2R,3R-difluoro)hexyloxy]-3-fluorobenzoate (Example 2a), can be accomplished by following the method of Example 2a with the exception that (2S,3R-epoxy)hexanol, a diastereomer of (2S,3S-epoxy)hexanol (XI, where $R_2$=propyl), is used in place of XI.

An alternate route of obtaining 4'-decyloxyphenyl-4-[(2R,3S-difluoro)hexyloxy]-3-fluorobenzoate follows. Initially, 4-decyloxyphenyl-4-[(2S,3S-epoxy)hexyloxy]-3-fluorobenzoate is synthesized by coupling p-decyloxyphenol with 4-[(2S,3S-epoxy)hexyloxy]-3-fluorobenzoyl chloride. Decyloxyphenol and 4-[(2S,3S-epoxy)hexyloxy]-3-fluorobenzoyl chloride are commercially available or can be synthesized by known methods from readily available starting materials. The p-decyloxyphenol is mixed with 4-[(2S,3S-epoxy)hexyloxy]-3-fluorobenzoyl chloride, dry methylene chloride, triethylamine and a few crystals of DMAP. The resulting mixture is stirred for 1 hour, after which the solvent is removed in vacuo. The residue is treated with aqueous HCl (5%, v/v) followed by extraction with ether. The combined ether layers are then washed sequentially with 5% aqueous HCl, 5% aqueous NaOH, and water and dried over anhydrous sodium sulfate. Removal of the solvent gives the crude intermediate product, 4-decyloxyphenyl-4-[(2S,3S-epoxy)hexyloxy]-3-fluorobenzoate, which can then be purified by flash chromatography using 9:1 (v/v) hexanes:ethyl acetate as eluent. The product can be further purified by recrystallization from ethanol.

Next, the 4-decyloxyphenyl-4-[(2S,3S-epoxy-hexyloxy]-3-fluorobenzoate is dissolved in methylene chloride, and the reaction solution cooled to 0° C. $(HF)_x$·pyridine is added and the resulting mixture is stirred for 15 minutes. The reaction is then quenched with water. Ethereal extractive workup results in a mixture of the fluorohydrin regioisomers.

The mixture of fluorohydrin regioisomers is dissolved in dry methylene chloride and cooled to −78° C., under argon. Diethylaminosulfurtrifluoride (DAST) is added dropwise to the cooled solution which is then stirred for ten minutes. The cooling bath is then removed after which the reaction is stirred for an additional hour. The reaction is then quenched with 10% (w/v) sodium bicarbonate. An ethereal extractive workup results in a mixtures of the diastereomers: the 2R,3R-difluoride and the 2R,3S-difluoride. The diastereomeric difluorides can then be separated and purified by flash chromatography on a silica gel (ethyl acetate:hexanes, 8%, v/v) in two fractions. The first fraction is the 2R,3S-difluoride, 4'-decyloxyphenyl-4-[(2R,3S-difluoro)hexyloxy]-3-fluorobenzoate. The second fraction is the 2R,3R-difluoride.

Example 3 Synthesis of 4'-$R_1$-phenyl-4-[(2-halo)alkoxy]-3-halobenzoates (XVI)

This example illustrates the synthesis of chiral nonracemic 4'-$R_1$-phenyl-4-[(2-halo)alkoxy]-3-halobenzoates (XVI) by the coupling of 4'-$R_1$-phenyl-3-halo-4-hydroxybenzoates with chiral 1-hydroxy-2-haloalkyls. The procedure is exemplified by the synthesis of the difluoro, 4'-n-decyloxyphenyl-4-[(4-methyl-2S-fluoro)-pentyloxy]-3-fluorobenzoate (XVI, where $R_1$=decyloxy, X and Z=F, and $R_2$=isopropyl).

Example 3a Synthesis of 4'-n-decyloxyphenyl-4-[(4-methyl-2S-fluoro)pentyloxy]-3-fluorobenzoate To produce 4'-n-decyloxyphenyl-4-[(4-methyl-2S-fluoro) pentyloxy]-3-fluorobenzoate, 4'-decyloxyphenyl-(4-hydroxy-3-fluoro)benzoate (X, where $R_1$=decyloxy and Z=F), 4-methyl-2S-fluoropentanol (XV, where X=F and $R_2$=isopropyl) (0.5 mmol) and triphenyl phosphine (0.75 mmol) were dissolved in dry THF and stirred with a magnetic stir bar for five minutes. Diisopropyl azodicarboxylate (1.5 equivalents) dissolved in dry THF, was allowed to drop in the reaction mixture at room temperature over a period of two hours. The reaction was further stirred with a stir bar overnight. The solvent was then rotoevaporated to dryness and the residue was subjected to flash chromatography on a silica column using 10% (v/v) ethyl acetate in hexanes to afford the product, 4'-n-decyloxyphenyl-4-[(4-methyl-2S-fluoro)pentyloxy]-3-fluorobenzoate in 84.3% yield. The product was further purified by crystallization from hexanes.

Example 3b Synthesis of 4'-n-decyloxyphenyl-4-[(4-methyl-2R-fluoro)pentyloxy]-3-fluorobenzoate To synthesize 4'-n-decyloxyphenyl-4-[(4-methyl-2R-fluoro)pentyloxy]-3-fluorobenzoate (XVI, where $R_1$=decyloxy, X and Z=F, and $R_2$=isopropyl), the method for Example 3b is followed with the exception that 4-methyl-2R-fluoropentanol is used in place of its enantiomer 4-methyl-2S-fluoropentanol (XV, where $R_2$=isopropyl).

Example 4 Synthesis of 4'-$R_1$-phenyl-4- [(1-methyl-2-halo) alkoxy ]-3 -halobenzoates This example illustrates the synthesis of chiral non-racemic 4'-$R_1$-phenyl-4-[(1-methyl-2-halo)alkoxy]-3-halobenzoates (XXII) by coupling of 4'-$R_1$-phenyl-3-halo-4-hydroxybenzoate (X) with a chiral 1-methyl-(2,3-epoxy)alkanol, opening the epoxy ring, followed by stereospecific halogenation of the resulting hydroxy group. The procedure is illustrated by the synthesis of the difluoride, 4'-n-decyloxyphenyl-4-[(1S,4-dimethyl-2S-fluoro)pentyloxy]-3-fluorobenzoate (XXII, where $R_1$=decyloxy, X and Z=F, and $R_2$=isopropyl) as illustrated by Scheme 6.

Example 4a Synthesis of 4'-decyloxyphenyl-4-[(1S,4-dimethyl-2S-fluoro)pentyloxy]-3-fluorobenzoate To produce 4'-decyloxyphenyl-4-[1S,4-dimethyl-(2S,3S-epoxy)-pentyloxy]-3-fluorobenzoate (XX, where $R_1$=decyloxy, Z=F and $R_2$=isopropyl), 0.64 mmol of 4'-decyloxyphenyl-(4-hydroxy-3-fluoro)benzoate (X, where $R_1$=decyloxy and Z =F), 0.65 mmol of 1R,4-dimethyl-(2S,3S-epoxy)-pentanol (XIX, where $R_2$=isopropyl) and triphenylphosphine were dissolved in dry THF in an argon filled flask. 1R,4-dimethyl-(2S,3S-epoxy)-pentanol was produced by the Mitsunobu reaction described in Example 4b. Diisopropyl azodicarboxylate dissolved in dry THF was added dropwise over a period of two hours while the mixture was stirred with a stir bar. The reaction mixture was further stirred overnight. The solvent was then rotoevaporated and the residue was subjected to flash chromatography on a silica column using an eluent of 5% (v/v) ethyl acetate in hexanes to afford the product, 4'-n-decyloxyphenyl-4-[1S,4-dimethyl-(2S,3S-epoxy)-pentyloxy]-3-fluorobenzoate (XX, where $R_1$=decyloxy, Z=F and $R_2$=isopropyl), in a 50% yield.

110 mg of 4'-decyloxyphenyl-4-[1S,4-dimethyl-(2S,3S-epoxy)-pentyloxy]-3-fluorobenzoate was dissolved in dry $CH_2Cl_2$ in an argon filled flask and cooled to 0° C. Morpholine borane complex (40 mg) and $BF_3$-$Et_2O$ (0.1 ml) were added and stirred with a stir bar for four hours until disappearance of the starting material. The reaction was then quenched with water and stirred for one hour at room temperature with a magnetic stir bar. Water (50 ml) was added and the organic layer was separated. The water layer was extracted twice with $CH_2Cl_2$. The combined organic layers were washed with brine, dried with $MgSO_4$, filtered and rotoevaporated. The residue was flash chromatographed with an eluent of 20% (v/v) ethyl acetate in hexanes on a silica column to afford 4'-decyloxyphenyl-4-[(1S,4-dimethyl-2R-hydroxy)pentyloxy]-3-fluorobenzoate (XXI, where $R_1$=decyloxy, Z=F and $R_2$=isopropyl) in 80% yield.

4'-decyloxyphenyl-4-[(1S,4-dimethyl-2R-hydroxy)-pentyloxy]-3-fluorobenzoate (85 mg) was dissolved in dry $CH_2Cl_2$ in a flame dried, argon filled flask and cooled to −70° C. Dimethylaminosulfurtrifluoride (DAST) (0.1 ml) was added to the cold solution. The reaction was stirred at −70° C. with a stir bar for four hours and then warmed to room temperature while stirring over a period of eighteen hours. The reaction was then quenched with cold $NaHCO_3$ solution and stirred for 15 minutes. The product was extracted with two 50 ml portions of $CH_2Cl_2$. Organic layers were combined and washed repeatedly with $NaHCO_3$ solution and brine, dried with $MgSO_4$, filtered and rotoevaporated. The residue was flash chromatographed on a silica column using 5% (v/v) ethyl acetate in hexanes to obtain the 20% yield of 4'-decyloxyphenyl-4-[(1S,4-dimethyl-2S-fluoro) pentyloxy]benzoate. The final product was further purified by crystallization from hexanes at −20° C.

Example 4b Synthesis of 1R,4-dimethyl-(2S,3S-epoxy)-pentanol

The synthesis of 1R,4-dimethyl-(2S,3S-epoxy)-pentanol (XIX, where $R_2$=isopropyl) is illustrated by Scheme 5. The epoxy alcohol, 1S,4-dimethyl-(2S,3S-epoxy)pentanol, (XVII, where $R_2$=isopropyl) (7.7 mmol), acetic acid (8 mmol) and triphenylphosphine (16 mmol) were dissolved in dry THF and a solution of diisopropyl azodicarboxylate (16 mmol) in dry THF was added dropwise over a period of three hours while stirred with magnetic stir bar. The reaction mixture was stirred overnight. The solvent was rotoevaporated and the residue was subjected to flash chromatography on a silica column using 4% (v/v) ethyl acetate in hexanes as eluent. The spot at $R_f$0.46 was collected in 50% yield. TLC resulted in two spots, $R_f$0.54 and 0.46. The second spot at $R_f$0.46 is the major product, the epoxy acetate of XVIII, where $R_2$=isopropyl. Since both spots are very close it is hard to completely separate the two diastereomers in a single flash chromatography procedure, although the overall yield of the epoxy acetate was high (86%).

The inverted acetate (200 mg) was dissolved in methanol (2 ml). Anhydrous $K_2CO_3$ (50 mg) was added and stirred with a stir bar at room temperature for half an hour. The completion of the reaction was judged by TLC. The solvent was carefully rotoevaporated and the residue was partitioned between ether and water fractions. The water layer was extracted twice with ether. Ether layers were combined, washed with diluted brine, dried over $MgSO_4$, filtered and rotoevaporated to obtain the 1R,4-dimethyl-2S,3S-epoxy pentanol (XIX, where $R_2$=isopropyl).

Example 4c Synthesis of 4'-decyloxyphenyl-4-[(1R,4-dimethyl-2R-fluoro)pentyloxy]-3-fluorobenzoate To synthesize 4'-decyloxyphenyl-4-[(1R,4-dimethyl-2R -fluoro) pentyloxy]-3-fluorobenzoate, i.e., the enantiomer of the composition produced by Example 4a, the method of Example 4a for the synthesis of 4'-decyloxyphenyl-4-[(1S,4-dimethyl-2S-fluoro)pentyloxy]-3-fluorobenzoate is followed with the exception that 1S,4-dimethyl-(2R,3R-epoxy)pentanol, the enantiomer of XIX ($R_2$=isopropyl), is used in place of compound XIX. The enantiomer of epoxy alcohol XIX can be synthesized by known methods from readily available starting materials.

Example 4d Synthesis of 4'-decyloxyphenyl-4-[(1R,4-dimethyl-2S-fluoro)pentyloxy]-3-fluorobenzoate To synthesize 4'-decyloxyphenyl-4-[(1R,4-dimethyl-2 S-Fluoro)pentyloxy]-3-fluorobenzoate, the diastereomer of 4'-decyloxyphenyl-4-[(1S,4-dimethyl-2S-fluoro)-pentyloxy]-3-fluorobenzoate (Example 4a), the method of Example 4a is followed with the exception that 1S,4-dimethyl-(2S,3S -epoxy)pentanol, XVII where $R_2$=isopropyl, is used in place of compound XIX. Compounds of formula XVII can be synthesized by known methods from readily available starting materials.

Example 5 Synthesis of Chiral 4'-R₁-phenyl-4-[(1-methyl-2,3-difluoro)alkoxy]-3-halobenzoates (XXV)

To synthesize 4'-R$_1$-phenyl-4-[(1-methyl-2,3-dihalo)alkoxy-3-halobenzoates, 4'-R$_1$-phenyl-4-hydroxy-3-halobenzoate (X) is coupled to a chiral 1-methyl-2-epoxy alkanol, the epoxy ring is opened and treated with a halogenating agent. The synthesis of 4'-R$_1$-phenyl-4-[(1-methyl-2,3-dihalo)alkoxy]-3-halobenzoates is exemplified by the synthesis of 4'-decyloxyphenyl-4-[(1S,4-dimethyl-2R,3R-difluoro)pentanyloxy]-3-fluorobenzoate (XXV, where R$_1$=decyloxy, X, Y and Z=F and R$_2$=isopropyl) as illustrated in Scheme 7.

Example 5a Synthesis of 4'-decyloxyphenyl-4- [(1S, 4-dimethyl-2R, 3R difluoro) pentanyloxy]-3-fluorobenzoate (MDW 205)

4'-decyloxyphenyl-(4-hydroxy-3-fluoro)benzoate (0.77 mmol), 1R,4-dimethyl-(2S,3S-epoxy)pentanol (XIX, R$_2$=isopropyl) (0.8 mmol) and triphenylphosphine (1.5 mmol) were dissolved in 10 ml of dry THF. A solution of DEAD (3 mmol) in 1 ml of dry THF was added dropwise over a period of two hours. The reaction mixture was stirred for two hours with a magnetic stir bar. The solvent was then taken off under vacuum and the residue was flash chromatographed using 5% (v/v) ethyl acetate in hexanes as eluent to afford the 4'-decyloxyphenyl-4-[(1S,4-dimethyl-2S,3S-epoxy)pentanyloxy]-3-fluorobenzoate (XXIII, where R$_1$=decyloxy, Z=F and R$_2$=isopropyl) in 44% yield.

190 mg (0.38 mmol) of the 4'-decyloxyphenyl-4-[(1S,4-dimethyl-2S,3S-epoxy)pentanyloxy]-3-fluorobenzoate was dissolved in 10 ml of dry CH$_2$Cl$_2$ and cooled to 0° C. 0.5 ml of HF in pyridine was added to the cold solution and stirred for one hour (completion of reaction measured by TLC). It was then quenched with cold water and stirred further for 15 minutes. The solvent was rotary evaporated and the residue was flash chromatographed on a silica column using 10% (v/v) ethyl acetate in hexanes to obtain 91% of the fluorohydrin product (XXIV, where R$_1$=decyloxy, X and Z=F and R$_2$=isopropyl).

In a flame dried argon filled flask, the fluorohydrin product (0.35 mmol) from above reaction, was dissolved in 20 ml of dry CH$_2$Cl$_2$ and cooled to −70° C. 0.1 ml of dimethyl aminosulfurtrifluoride (DAST) was added to the reaction mixture and was allowed to stir for two hours at −70° C. The reaction mixture was stored in the refrigerator overnight. It was quenched with cold NaHCO$_3$ solution and stirred for 15 minutes. The product was extracted in CH$_2$Cl$_2$ (two 50 ml portions). Organic layers were combined and washed repeatedly with NaHCO$_3$ solution and brine, dried with MgSO$_4$, filtered and rotary evaporated. The residue was flash chromatographed on a silica column using 5% (v/v) ethyl acetate in hexanes to obtain 49% yield. The final product, 4'-decyloxyphenyl-4-[(1S,4-dimethyl-2R,3R-difluoro)pentanyloxy]-3-fluorobenzoate (XXV, where R$_1$=decyloxy, X, Y and Z =F and R$_2$=isopropyl), was further purified by crystallization from hexanes.

Example 5b Synthesis of 4'-decyloxyphenyl-4- [(1R, 4 4-dimethyl-2S, 3S-difluoro) pentanyloxy]-3-fluorobenzoate To synthesize 4'-decyloxyphenyl-4-[(1R,4-dimethyl-2S,3S-difluoro)pentanyloxy]-3-fluorobenzoate, the procedure of Example 5a is followed with the exception that 1S,4-dimethyl-(2R,3R-epoxy)pentanol is used in place of 1R,4-dimethyl-(2S,3S -epoxy)pentanol (XIX, R$_2$=isopropyl). 1S,4-dimethyl-(2R,3R-epoxy)pentanol is commercially available or can be synthesized by known methods from readily available starting materials.

Example 5c Synthesis of 4'-decyloxyphenyl-4- [1R, 4-dimethyl-2R, 3R-difluoro) pentanyloxy]-3-fluorobenzoate (MDW235)

The synthesis of 4'-decyloxyphenyl-4-[1R,4-dimethyl-2R,3R-difluoro) pentanyloxy]-3-fluorobenzoate, a diastereomer of 4'-decyloxyphenyl-4-[1S,4-dimethyl-2R,3R-difluoro)pentanyloxy]-3-fluorobenzoate (Example 5a), the method of Example 5a was followed with the exception that 1S,4-dimethyl-(2S,3S-epoxy)pentanol (XVII, R$_2$=isopropyl) was used in place of 1R,4-dimethyl-(2S,3S-epoxy)pentanol (XIX, R$_2$=isopropyl).

4'-decyloxyphenyl-(4-hydroxy-3-fluoro)benzoate (1.0 mmol), 1S,4-dimethyl-(2S,3S-epoxy)pentanol (XVII, where R$_2$=isopropyl) (1.0 mmol) and triphenylphosphine (1.5 mmol) were dissolved in 10 ml of dry THF. A solution of diisopropyl azodicarboxylate (3 mmol) in 1 ml of dry THF was added dropwise over a period of two hours. The reaction mixture was stirred for two hours with a magnetic stirring bar. The solvent was then taken off under vacuum and the residue was flash chromatographed using 5% (v/v) ethyl acetate in hexanes as eluent to afford the 4'-decyloxyphenyl-4-[(1R,4-dimethyl-2S, 3S-epoxy)pentanyloxy]-3-fluorobenzoate product (MDW207) in 84% yield.

240 mg (0.52 mmol) of the 4'-decyloxyphenyl-4-[(1R,4-dimethyl-2S,3S-epoxy)pentanyloxy]-3-fluorobenzoate was dissolved in 10 ml of dry CH$_2$Cl$_2$ and cooled to 0° C. 0.5 ml of HF in pyridine was added to the cold solution and stirred for one hour with a stirring bar. Completion of the reaction was determined by TLC. It was then quenched with cold water and stirred further for 15 minutes. The solvent was rotary evaporated and the residue was flash chromatographed on a silica column using 10% (v/v) ethyl acetate in hexanes to obtain 82% of the fluorohydrin product.

In a flame dried argon filled flask the fluorohydrin product (208 mg) from the above reaction, was dissolved in 20 ml of dry CH$_2$Cl$_2$ and cooled to −70° C. 0.1 ml of dimethyl aminosulfurtrifluoride (DAST) was added to the reaction mixture and was allowed to stir for two hours at −70° C. The reaction mixture was stored in the refrigerator overnight. It was quenched with cold NaHCO$_3$ solution and stirred for 15 minutes. The product was extracted in CHCl$_2$ (two 50 ml portions). Organic layers were combined and washed repeatedly with NaHCO$_3$ solution and brine, dried with MgSO$_4$, filtered and rotary evaporated. The residue was flash chromatographed on a silica column using 5% ethyl acetate in hexanes to obtain 45% yield. The final product, 4'-decyloxyphenyl-4-[1R,4-dimethyl-2R,3R-difluoro)pentanyloxy]-3-fluorobenzoate was further purified by crystallization from hexanes.

Example 6 Synthesis of 2-[4-(2,3-dihaloalkoxy)-2,3-dihalo]phenyl-5-$R_1$-pyrimidines.

Example 6a Synthesis of 2-[4-(2R,3R-difluorohexyloxy)-2,3-difluoro]phenyl-5-octylpyrimidine (MDW 434)

The synthesis of 2-[4-(2R,3R-difluorohexyloxy)-2,3-difluoro]phenyl-5-octyl-pyrimidine (MDW 434) was carried out as described above, except that 2-(2,3-difluoro-4-hydroxy)phenyl-5-octylpyrimidine was used in place of 4'-$R_1$-phenyl-3-halo-4-hydroxy-benzoate (X) in Scheme 3. 2-(2,3-difluoro-4-hydroxy)-phenyl-5-octyl-pyrimidine is commercially available or can be synthesized by routine modifications of methods disclosed herein or by methods known in art.

To join the chiral tail to the core, 2S,3S-epoxyhexanol was reacted with 2-(2,3-difluoro-4-hydroxy)phenyl-5-octylpyrimidine by a routine modification of the method illustrated in Scheme 3. The epoxy group was then converted to 2R,3R-difluoro by the method described in Example 2a.

Example 6b Synthesis of 2-[4-(2R,3R-difluorohexyloxy)-2,3-difluoro]phenyl-5-octyloxypyrimidine (MDW 433)

The synthesis of 2-[4-(2R,3R-difluorohexyloxy)-2,3-difluoro]phenyl-5-octyloxypyrimidine (MDW 433) was carried out as described above, except that 2-(2,3-difluoro-4-hydroxy)-phenyl-5-octyloxypyrimidine was used in place of 4'-$R_1$-phenyl-3-halo-4-hydroxy-benzoate (X) in Scheme 3. 2-(2,3-difluoro-4-hydroxy)phenyl-5-octyloxypyrimidine is commercially available or can be synthesized by routine modifications of methods disclosed herein or by methods known in art.

To join the chiral tail to the core, 2S,3S-epoxyhexanol was reacted with 2-(2,3-difluoro-4-hydroxy)phenyl-5-octyloxypyrimidine by a routine modification of the method illustrated in Scheme 3. The epoxy group was then converted to 2R,3R-difluoro by the method described in Example 2a.

Example 7 Synthesis of 2-[4-(2,3-dihaloalkoxy)-2,3-dihalo]phenyl-5-$R_1$-pyridines.

Example 7a Synthesis of 2-[4-(2R,3R-difluorohexyloxy)-2,3-difluoro]phenyl-5-octylpyridine (MDW 585)

The synthesis of 2-[4-(2R,3R-difluorohexyloxy)-2,3-difluoro]phenyl-5-octyl-pyridine (MDW 585) was carried out as described above, except that 2-(2,3-difluoro-4-hydroxy)phenyl5-octylpyridine was used instead of 4'-$R_1$-phenyl-3-halo-4-hydroxy-benzoate (X) in Scheme 3. 2-(2,3-difluoro-4-hydroxy)phenyl-5-octylpyridine is commercially available or can be synthesized by routine modifications of methods described herein or known in the art.

To join the chiral tail to the core, 2S,3S-difluorohexanol was reacted with 2-(2,3-difluoro-4-hydroxy)phenyl-5-octylpyridine by a routine modification of the method illustrated in Scheme 3. The epoxy group was then converted to 2R,3R-difluoro by the method described in Example 2a.

Example 7b Synthesis of 2-[4-(2R,3R-dihalohexyloxy)-2,3-difluoro]phenyl-5-octyloxypyridine The synthesis of 2-[4- (2R, 3R-dihalohexyloxy) -2,3-difluoro]-phenyl-5-octyloxy-pyridine can be carried out by methods described herein, with the exception that 2-(2,3-difluoro-4-hydroxy)phenyl-5-octyloxypyridine is used instead of 4'-$R_1$-phenyl-3-halo-4-hydroxy-benzoate (X) in Scheme 3. 2-(2,3-difluoro-4-hydroxy) phenyl-5-octyloxypyridine is commercially available or can be synthesized by routine modifications of methods described herein or known in the art.

To join the chiral tail to the core, 2S,3S-epoxyhexanol is reacted with 2-(2,3-difluoro-4-hydroxy)phenyl-5-octyloxypyridine by a routine modification of the method illustrated in Scheme 3. The epoxy group is then converted to 2R,3R-difluoro by the method described in Example 2a.

Example 8 Synthesis of 2-[3-halo-4-(2,3-dihalo)alkoxy]-phenyl-5-$R_1$-pyrimidines.

Example 8a Synthesis of 2-[3-fluoro-4-(2R,3R-difluoro)-alkoxy]phenyl-5-octyloxypyrimidine (MDW 427)

The synthesis of 2-[3-fluoro-4-(2R,3R-difluoro)alkoxy]phenyl-5-octyloxypyrimidine was carried out by methods described herein, except that 2-(3-fluoro-4-hydroxy)phenyl-5-octyloxypyrimidine was used instead of 4'-$R_1$-phenyl-3-halo-4hydroxybenzoate (X) in Scheme 3. 2-(3-fluoro-4-hydroxy)phenyl-5-octyloxypyrimidine is commercially available or can be synthesized by routine modification of methods described herein or by methods known in the art.

To join the chiral tail to the core, 2S,3S-epoxyhexanol was reacted with 2-(3-fluoro-4-hydroxy)phenyl-5-octyloxypyrimidine by a routine modification of the method illustrated in Scheme 3. The epoxy group was then converted to 2R,3R-difluoro by the method described in Example 2a.

Example 9 Synthesis of 2-[3-halo-4-(2,3-dihalo)alkoxy]-phenyl-5-$R_1$-pyridines.

Example 9a Synthesis of 2-[3-fluoro-4-(2R,3R-difluoro)-alkoxy]phenyl-5-octyloxypyridine The synthesis of 2-[3-fluoro-4-(2R,3R-difluoro)-alkoxy]phenyl-5-octyloxypyridine was carried out by methods described herein, except that 2-(3-fluoro-4-hydroxy)phenyl-5-octyloxypyridine was used instead of 4'-$R_1$-phenyl-3-halo-4-hydroxybenzoate (X) in Scheme 3. 2-(3-fluoro-4-hydroxy)phenyl-5-octyloxypyridine is commercially available or can be synthesized by routine modification of methods described herein or by methods known in the art.

To join the chiral tail to the core, 2S,3S-epoxyhexanol was reacted with 2-(3-fluoro-4-hydroxy)phenyl-5-octyloxypyridine by a routine modification of the method illustrated in Scheme 3. The epoxy group was then converted to 2R,3R-difluoro by the method described in Example 2a.

This invention has been described and illustrated by reference to several preferred embodiments, but it is not intended to limit the invention by doing so. It is intended that the invention encompass all enantiomers and regioisomers of the general formula:

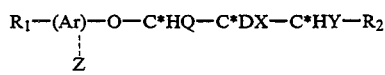

It is also intended that the invention include mixtures of two or more compositions of the subject invention, and FLC formulations in which these compounds are admixed with each other or with other compounds including LC and FLC materials.

We claim:

1. A chiral nonracemic compound of the general formula:

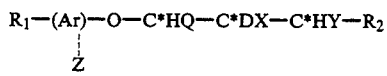

wherein:
* denotes a chiral or potentially chiral carbon,
$R_1$ is an achiral alkoxy group of two to sixteen carbons,
$R_2$ comprises the distal segment of the chiral tail and has one to ten carbons,
X is a halide and Y is H or a halide,
Q and D are H or methyl, provided that Q and D are not both methyl,
the —O—C*HQ—C*DX—C*HY— segment comprises the chiral proximal segment of the chiral tail, and is selected from the diastereomers and enantiomers:
2S-halo,2R-halo,
1S-methyl-2S-halo, 1R-methyl-2R-halo,
1S-methyl-2R-halo, 1R-methyl-2S-halo,
2S,3S-dihalo, 2R,3R-dihalo
2R,3S-dihalo, 2S,3R-dihalo,
1R-methyl-2R,3R-dihalo, 1S-methyl-2S,3S-dihalo,
1R-methyl-2R,3S-dihalo. 1S-methyl-2S,3R-dihalo,
1R-methyl,2S,3S-dihalo, 1S-methyl-2R,3R-dihalo,
1R-methyl-2S,3R-dihalo, and 1S-methyl-2R,3S-dihalo,
Ar is an FLC core of two or three aromatic rings, and Z is a halide located ortho relative to the chiral proximal tail.

2. The compound of claim 1 wherein Y is a halide and Q and D are H.

3. The compound of claim 1, wherein Ar is selected from the group consisting of, phenylpyrimidine, phenylpyridine, (phenyl)phenylpyrimidine, (phenyl)phenylpyridine, phenylbenzoate, (phenyl)phenylbenzoate, and terphenyl.

4. The compound of claim 1 wherein the chiral proximal segment is selected from the enantiomers: 2R,3R-dihalo 2S,3S-dihalo.

5. The compound of claim 1 wherein Y is a halide, Q and D are H, Ar is phenylpyridine or phenylpyrimidine, and the chiral proximal segment is selected from the enantiomers: 2R,3R-dihalo and 2S,3S-dihalo.

6. A chiral nonracemic compound of the formula:

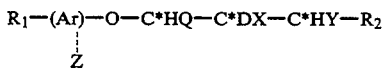

wherein:
* denotes a chiral or potentially chiral carbon,
$R_1$ is a achiral alkyl or alkenyl group of two to sixteen carbons,
$R_2$ comprises the distal segment of the chiral tail and has one to ten carbons,
X is a halide and Y is H or a halide, and Q and D are methyl or H, provided that Q and D are not both methyl,
the chiral proximal tail —O-13 C*HQ—C*DX—C*Hy segment comprises a diastereomer or enantiomer selected from the group consisting of:
2S-halo,2R-halo,
1S-methyl-2S-halo, 1R-methyl-2R-halo,
1S-methyl-2R-halo, 1R-methyl-2S-halo,
2S,3S-dihalo, 2R,3R-dihalo,
2R,3S-dihalo, 2S,3R-dihalo,
1R-methyl-2R,3S-dihalo, 1S-methyl-2S,3S-dihalo,
1R-methyl-2R,3S-dihalo, 1S-methyl-2S,3R-dihalo,
1R-methyl-2S,3S-dihalo, 1S-methyl-2R,3R-dihalo,
1R-methyl,2S,3R-dihalo, and 1S-methyl-2R,3S-dihalo,
Ar is an FLC core of two or three aromatic rings, and Z is a halide located ortho relative to the chiral proximal tail except that when Ar is phenylpyrimidine or phenylpyridine the chiral proximal tail cannot be 2S,3S-dihalo, 2R,3R-dihalo, 2R,3S-dihalo or 2S,3R-dihalo.

7. The compound of claim 6 wherein Y is a halide and Q and D are H.

8. The compound of claim 6 wherein Ar is selected from the group consisting of phenylpyrimidine, phenylpyridine, (phenyl)phenylpyrimidine, (phenyl)phenylpyridine, phenylbenzoate, (phenyl)phenylbenzoate, and terphenyl.

9. The compound of claim 6 wherein the chiral proximal segment is selected from the enantiomers: 2R,3R-dihalo 2S,3S-dihalo.

10. A chiral nonracemic compound of the formula:

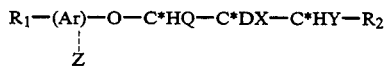

wherein:
*denotes a chiral or potentially chiral carbon,
$R_1$ is an achiral alkyl, alkenyl or alkoxy group of two to sixteen carbons,
$R_2$ comprises the distal segment of the chiral tail and has one to ten carbons,
X is a halide, Y is H or a halide, and Q and D are H or a methyl group, provided that Q and D are not both methyl,
the —O—C*HO—C*DX—C*HY segment comprises the chiral proximal segment of the chiral tail, and is selected from the diastereomers or enantiomers:
2S-halo, 2R-halo, 1S-methyl-2S-halo, 1R-methyl-2R-halo,
1S-methyl-2R-halo, 1R-methyl-2S-halo,
2S,3S-dihalo, 2R,3R-dihalo,
2R,3S-dihalo, 2S,3R-dihalo,
1R-methyl-2R,3R-dihalo, 1S-methyl-2S, 3S-dihalo,
1R-methyl-2S,3S-dihalo, 1S-methyl-2R,3R-dihalo,
1R-methyl-2S,3R-dihalo, and 1S-methyl-2R,3S-dihalo,
Ar comprises a two or three ring aromatic core, and Z is two halides located ortho and meta relative to the chiral proximal tail.

11. The compound of claim 10 wherein Y is a halide and Q and D are H.

12. The compound of claim 10 wherein Ar is selected from the group consisting of phenylpyrimidine, phenylpryidine, (phenyl)phenylpryimidine, (phenyl)phenylpyridine, phenylbenzoate, (phenyl)phenylbenzoate, and terphenyl.

13. The compound of claim 10, wherein the chiral proximal segment is selected from the enantiomers: 2R,3R-dihalo 2S,3S-dihalo.

14. The compound of claim 10, wherein Q is H, D is methyl and Y is H.

15. A chiral nonracemic compound of the formula:

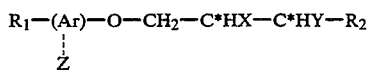

wherein:
* denotes a chiral carbon,
$R_1$ is an achiral alkyl, alkenyl or alkoxy group of two to sixteen carbons,
$R_2$ comprises the distal segment of the chiral tail and has one to ten carbons,
Ar is a phenylpyrimidine or phenylpyridine,
Z is two halides located ortho and meta relative to the chiral proximal tail,
and the —O—CH$_2$—C*HX—C*HY— segment is selected from the diastereomers and enantiomers:
2R, 3R-dihalo and 2S, 3-dihalo or
2R, 3S-dihalo and 2S, 3R-dihalo.

16. The compound of claim 15 wherein the —O—CH$_2$—C*HX—C*HY— segment is selected from the enantiomers: 2R, 3R-dihalo and 2S, 3S-dihalo.

17. The compound of claim 16 wherein Ar is a phenylpyrimidine.

18. The compound of claim 16 wherein Ar is a phenylpyridine.

19. The compound of claim 16 wherein X and Y, independently of one another, are either fluorine or chlorine.

20. The compound of claim 16 wherein X and Y are both fluorines.

21. The compound of claim 16 wherein Z is fluorine.

22. A chiral nonracemic compound of the formula:

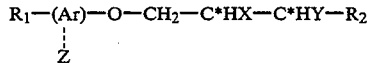

wherein:
* denotes a chiral carbon,
$R_1$ia an achiral alkyl, alkenyl or alkoxy group of two to sixteen carbons,
$R_2$ comprises the distal segment of the chiral tail and has one to ten carbons,
Ar is a three-ring core selected from the group of cores:

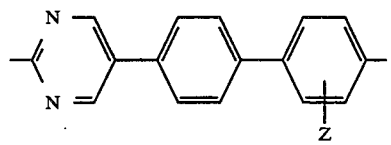

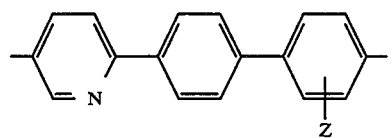

-continued

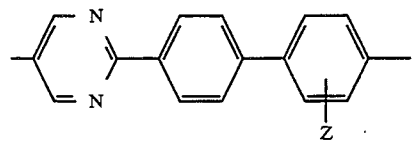

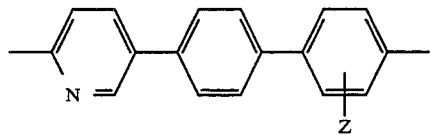

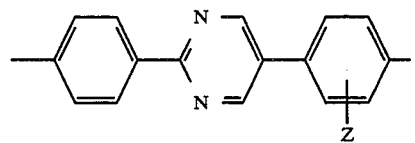

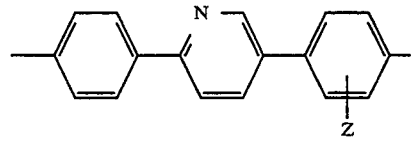

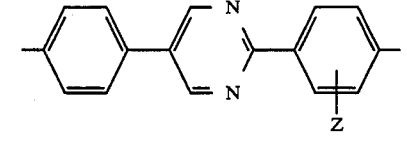

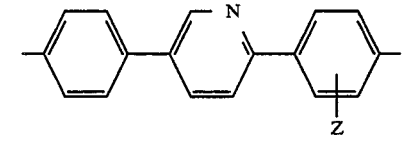

Z is either a single halide located ortho to the chiral proximal tail or two halides located ortho and meta relative to the chiral proximal tail, and the —O—CH$_2$—C*HX—C*HY— segment is selected from the diastereomers and enantiomers:
2R, 3R-dihalo and 2S, 3S-dihalo or 2R, 3S-dihalo and 2S, 3R-dihalo.

23. The compound of claim 22 wherein the —O—CH$_2$—C*HX—C*HY— segment is selected from the enantiomers 2R, 3R-dihalo and 2S, 3S-dihalo.

24. The compound of claim 23 wherein Z is two halides located ortho and meta relative to the chiral proximal tail.

25. The compound of claim 24 wherein X and Y, independently of one another, are either fluorine or chlorine.

26. The compound of claim 25 wherein X and Y are both fluorines.

27. The compound of claim 26 wherein Z is fluorine.

28. The compound of claim 6 wherein Ar is a three-ring core selected from the cores:

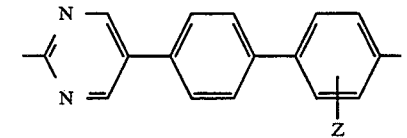

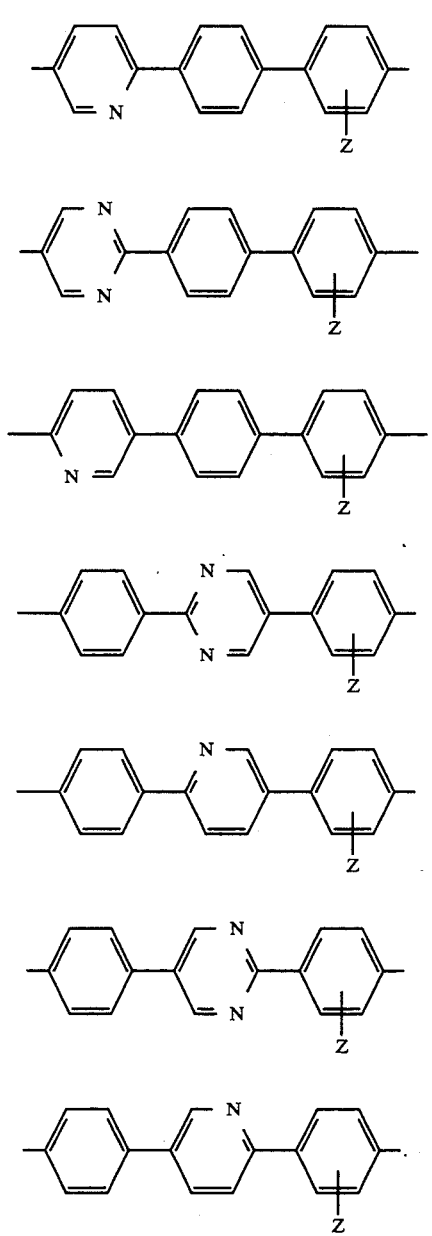
29. The compound of claim 10 wherein Ar is a three-ring core selected from the cores:
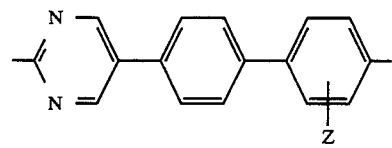
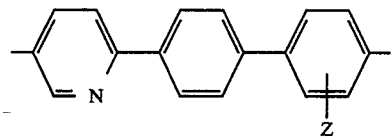
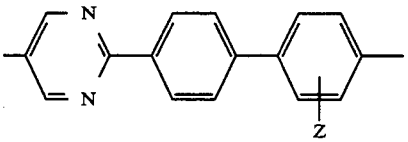
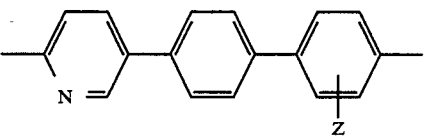
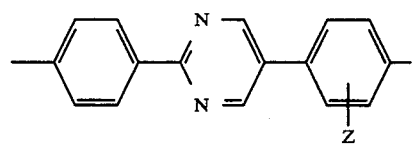
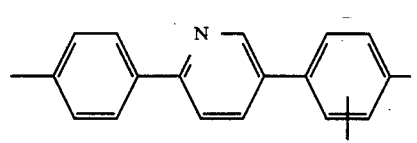
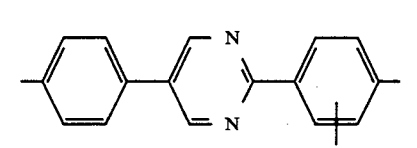
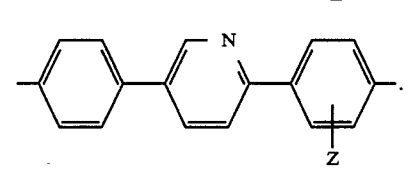
* * * * *

UNITED STATES PATENT AND TRADEMARK OFFICE
CERTIFICATE OF CORRECTION

PATENT NO. : 5,422,037

DATED : June 6, 1995

INVENTOR(S) : Wand, Michael et al.

It is certified that error appears in the above-indentified patent and that said Letters Patent is hereby corrected as shown below:

Column 15 at the top of the column above the chemical formulas, please insert --Scheme 2:--

Column 17 near top of column, please replace existing formula XIX with

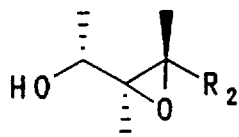

Column 41, line 28 in claim 1, please rewrite "2S-halo,2R-halo" as --2S-halo, 2R-halo--.

Column 42, line 4 in claim 6, please rewrite "-O-13 C*HQ-C*DX-C*Hy" as -- -O-C*HQ-C*DX-C*HY --.

Column 42, line 7 in claim 6, please rewrite "2S-halo,2R-halo" as --2S-halo, 2R-halo--.

UNITED STATES PATENT AND TRADEMARK OFFICE
CERTIFICATE OF CORRECTION

PATENT NO. : 5,422,037
DATED : January 19, 1993
INVENTOR(S) : Wand, Michael et al.

It is certified that error appears in the above-indentified patent and that said Letters Patent is hereby corrected as shown below:

Column 42, line 49 in claim 10, please rewrite "-O-C*HO-C*DX-C*HY" as -- -O-C*HQ-C*DX-C*HY --.

Signed and Sealed this

Nineteenth Day of December, 1995

Attest:

BRUCE LEHMAN

Attesting Officer

Commissioner of Patents and Trademarks